US011627970B2

(12) United States Patent
Hopkinson et al.

(10) Patent No.: US 11,627,970 B2
(45) Date of Patent: Apr. 18, 2023

(54) INFLATABLE SURGICAL COMPRESSION DEVICE AND RELATED SYSTEMS AND METHODS

(71) Applicant: Merit Medical Systems, Inc., South Jordan, UT (US)

(72) Inventors: Aaron Hopkinson, Herriman, UT (US); Jim Mottola, West Jordan, UT (US); Stephanie Chard, Salt Lake City, UT (US); Michael Hallisey, Wethersfield, CT (US)

(73) Assignee: Merit Medical Systems, Inc., South Jordan, UT (US)

(*) Notice: Subject to any disclaimer, the term of this patent is extended or adjusted under 35 U.S.C. 154(b) by 0 days.

(21) Appl. No.: 17/127,640

(22) Filed: Dec. 18, 2020

(65) Prior Publication Data

US 2021/0186519 A1 Jun. 24, 2021

Related U.S. Application Data

(60) Provisional application No. 63/111,437, filed on Nov. 9, 2020, provisional application No. 62/951,741, filed on Dec. 20, 2019.

(51) Int. Cl.

| | |
|---|---|
| ***A61B 17/135*** | (2006.01) |
| ***A61B 17/00*** | (2006.01) |
| *A61N 1/375* | (2006.01) |
| *A61B 17/12* | (2006.01) |

(52) U.S. Cl.

CPC .. *A61B 17/135* (2013.01); *A61B 2017/00893* (2013.01); *A61B 2017/12004* (2013.01); *A61N 1/375* (2013.01)

(58) Field of Classification Search

CPC ................ A61B 17/132; A61B 17/135; A61B 2017/00893

See application file for complete search history.

(56) References Cited

U.S. PATENT DOCUMENTS

| | | | | |
|---|---|---|---|---|
| 5,514,155 | A * | 5/1996 | Daneshvar | A61B 17/1325 602/53 |
| 2007/0260162 | A1 | 11/2007 | Meyer et al. | |
| 2007/0282239 | A1 | 12/2007 | Bates et al. | |
| 2019/0069905 | A1* | 3/2019 | Pancholy | A61B 5/0261 |
| 2019/0133602 | A1 | 5/2019 | Kiemeneij et al. | |
| 2019/0290288 | A1* | 9/2019 | Popp | A61B 17/1325 |

FOREIGN PATENT DOCUMENTS

| | | |
|---|---|---|
| CN | 207545157 | 6/2018 |
| JP | 07008500 | 1/1995 |

OTHER PUBLICATIONS

International Search Report and Written Opinion dated Apr. 22, 2021 for PCT/US2020/066210.

* cited by examiner

*Primary Examiner* — Sarah A Simpson
*Assistant Examiner* — Raihan R Khandker
(74) *Attorney, Agent, or Firm* — Dorsey & Whitney LLP

(57) ABSTRACT

Inflatable compression devices are disclosed. In some embodiments the devices provide compression to the torso of a patient, including at a pocket configured to receive a pacing device. In some embodiments at least one securing strap is displaceable with respect to a compression member. In some embodiments a compression member is displaceable relative to at least one securing strap.

18 Claims, 18 Drawing Sheets

100 120 125 60 50 150 110

60
150
110
125
120
50
100

INFLATABLE SURGICAL COMPRESSION DEVICE AND RELATED SYSTEMS AND METHODS

RELATED APPLICATIONS

This application claims priority to U.S. Provisional Application No. 62/951,741, filed on Dec. 20, 2019 and titled "Inflatable Surgical Compression Device and Related Systems and Methods" and to U.S. Provisional Application No. 63/111,437, filed on Nov. 9, 2020 and titled "Inflatable Surgical Compression Device and Related Systems and Methods" both of which are hereby incorporated by reference in their entireties.

TECHNICAL FIELD

The present disclosure relates generally to medical devices used to provide hemostasis and/or compression to a vascular puncture or wound site as well as related systems and methods. More particularly, some embodiments of the present disclosure relate to inflatable compression devices, systems, and methods used to provide hemostasis at surgical site, including surgical sites located on the torso.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
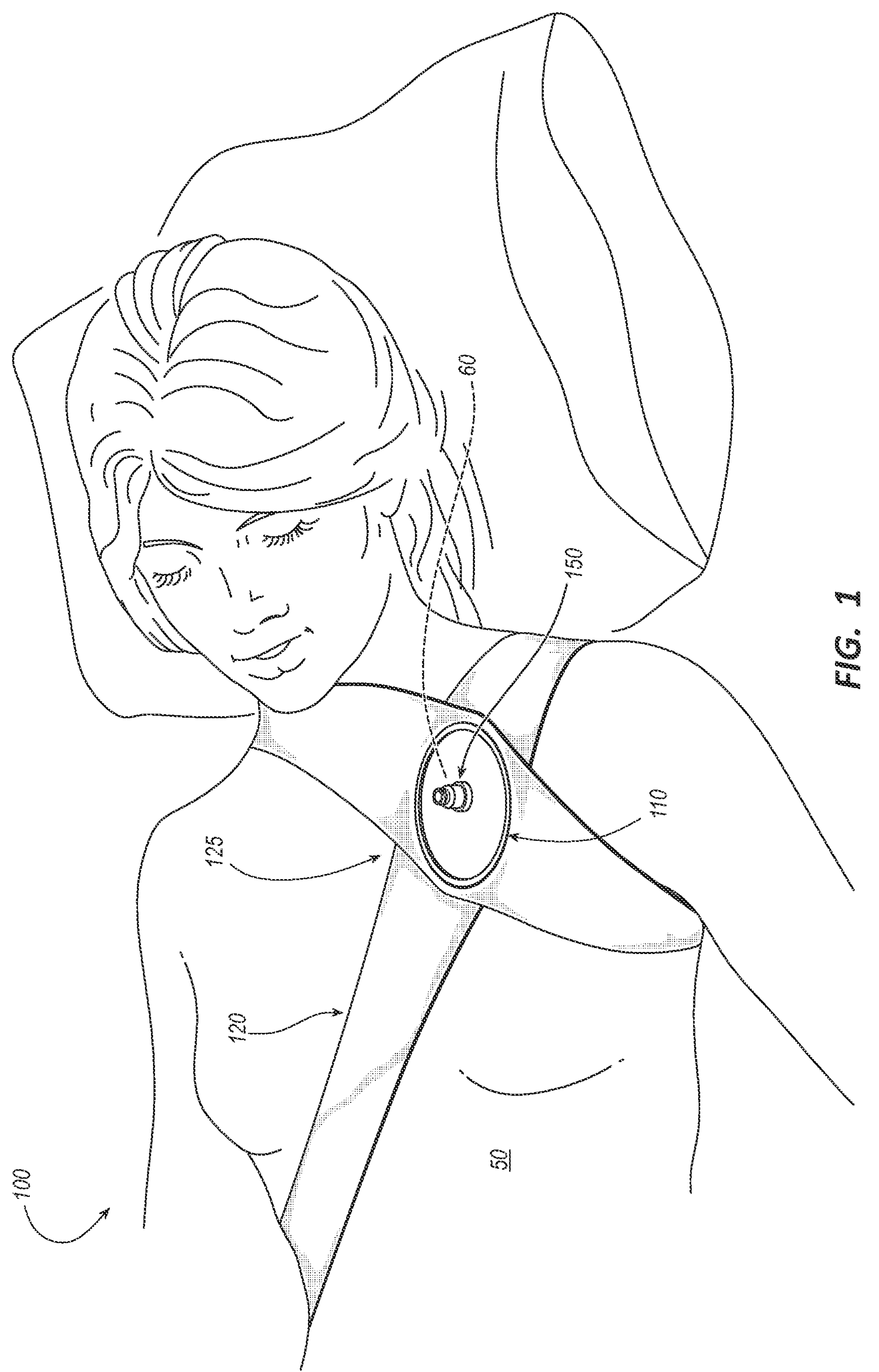
FIG. 1 is an illustration of an inflatable compression device in use on a patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic interaction. Thus, two components may be coupled to each other even though they are not in direct contact with each other. The phrase "fluid communication" is used in its ordinary sense and is broad enough to refer to arrangements in which a fluid (e.g., a gas or a liquid) can flow from one element to another element when the elements are in fluid communication with each other.

The term "fluid" is used in its broadest sense, to refer to any fluid, including both liquids and gases as well as solutions, compounds, suspensions, etc., which generally behave as fluids.

The term "compression" is used to define a compressive force or pressure applied to a portion of a patient over an area. The compression level may correlate to a pressure within an inflatable component of a compression device. The compression level may also correlate to a volumetric size or shape of an inflatable component. The compression level may also correlate to a downward force of the compression device.

The term "inflation" refers to the condition of an expandable fluid container. An increase of inflation correlates to an increase in fluid content within the container or to the volumetric size of the container. The inflation fluid may be compressible or non-compressible. The inflation level may or may not correlate to an internal pressure.

In some instances, surgery may cause some internal and/or external bleeding at or near the surgical site. This may lead to unwanted blood loss, development of hematoma, or other undesired outcomes. Thus, control of bleeding and/or establishing hemostasis may be part of a variety of treatments and procedures. In some instances, application of compression at an incision site may reduce the amount of bleeding and establish hemostasis after surgery.

The placement of pacing devices, such as a pacemaker or defibrillator, within a patient may include surgical creation of a pocket to receive the pacing device. Such a pocket may be formed in the tissue under the patient's skin on the torso of the patient, for example on the upper part of the patient's chest near the pectoral muscle and/or collarbone. In some instances, the external incision associated with creation of the pocket may be between one and three inches long. Creation of the pocket may cause internal and/or external bleeding and, in some instances, application of compression to the surgical site may reduce or otherwise aid in controlling the bleeding.

In some therapies, a pacing device may be located adjacent or near the subclavian or brachial vein and may include one or more pacemaker leads extending to the heart through the vasculature, such as through one of the subclavian or brachial veins. Again, the pacing device may also be disposed within a pocket in the tissue of the patient. Surgical incisions and tissue removal may thus create a surgical or incision site, which may also be referred to herein as the compression site, as application of compression may aid in controlling bleeding of the surgical or incision site after surgery. In some instances, compression may be applied for a few hours or for days. Inflatable compression devices as described herein may be configured to provide compression to the compression site.

The application of compression to certain sites on the human body may present some difficulty. Applying compression around a relatively small extremity such as a wrist or lower leg may be facilitated by straps extending around a relatively small circumference. In such instances, straps may be wrapped completely around the extremity so as to create a tension in the straps which may be translated to a downward force on a compression device. Sites on the body where a full wrap-around approach is not feasible may need to rely on attachment of the straps to the skin surface. Furthermore, body sites having a large radius of curvature, such as the torso, may cause further complications in establishing a downward force on a compression device without the compression device having to protrude away from the body surface. Further, on some areas of the body, the skin may be substantially loose and thereby be prone to lateral displacement. As such, the skin may easily stretch or laterally displace in the direction of a strap resulting in loss or decrease in strap tension. Systems and methods as described herein may serve to minimize and/or overcome these complications in establishing a compression force to a compression site on the torso of a human body.

FIG. 1 is an illustration of an embodiment of an inflatable compression device 100 in use on a patient 50. The compression device 100 may be configured to provide a variable compressive pressure to a compression site 60. The compression device 100 may comprise a compression member 110 and a securement system 120. The securement system 120 may be coupled to the compression member 110 and be configured to facilitate attachment of the compression member 110 to a patient 50 so as to be over a compression site 60. The securement system 120 may be configured to provide positional stability of the compression member 110 over the compression site 60. The securement system 120 may comprise a plurality of straps 125 extending away from the compression member 110. The compression member may comprise an inflation port 150 as further described below.

Figure 2:
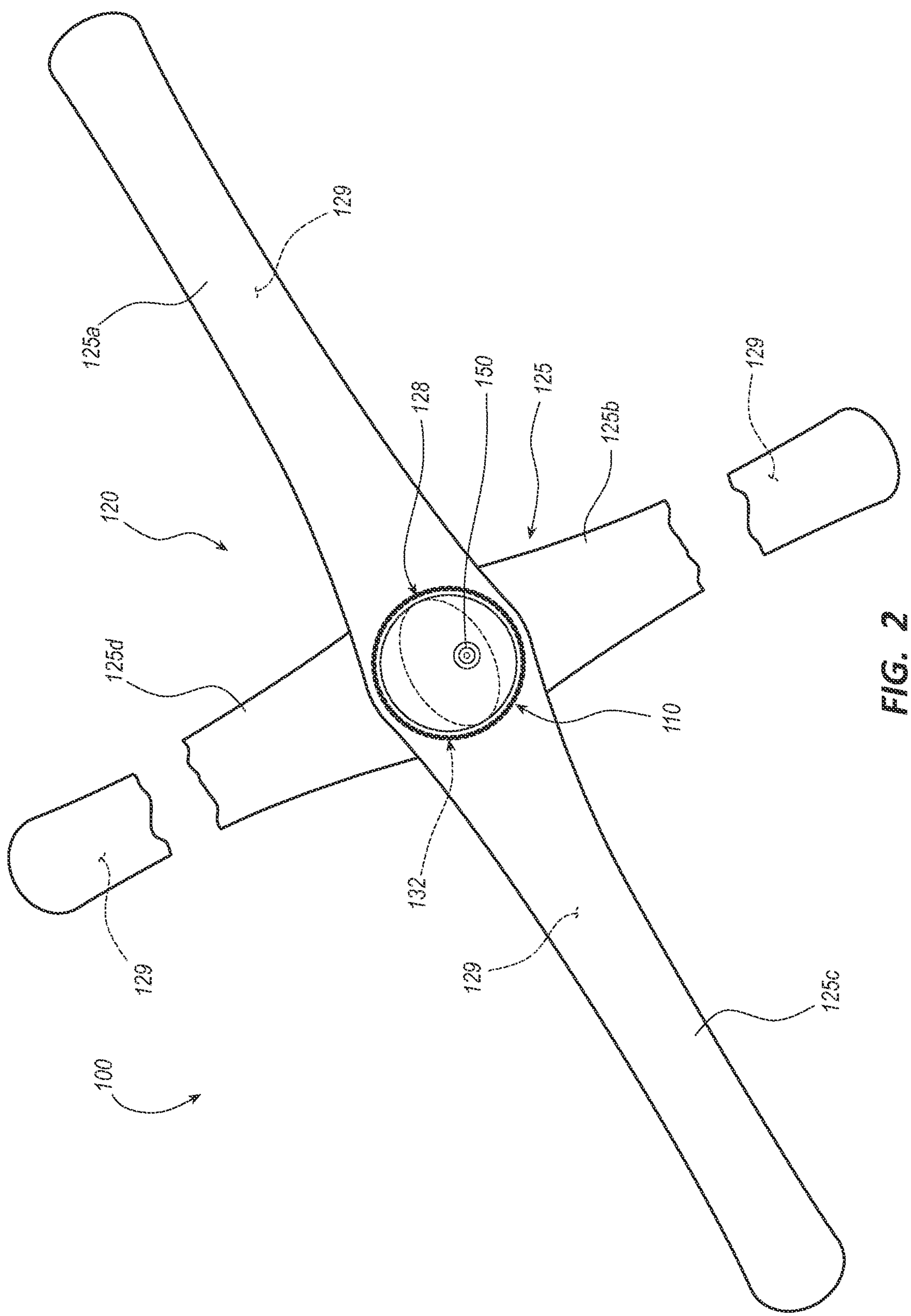
FIG. 2 is a top view of the inflatable compression device of FIG. 1 with the straps in a first configuration.
Figure 3:
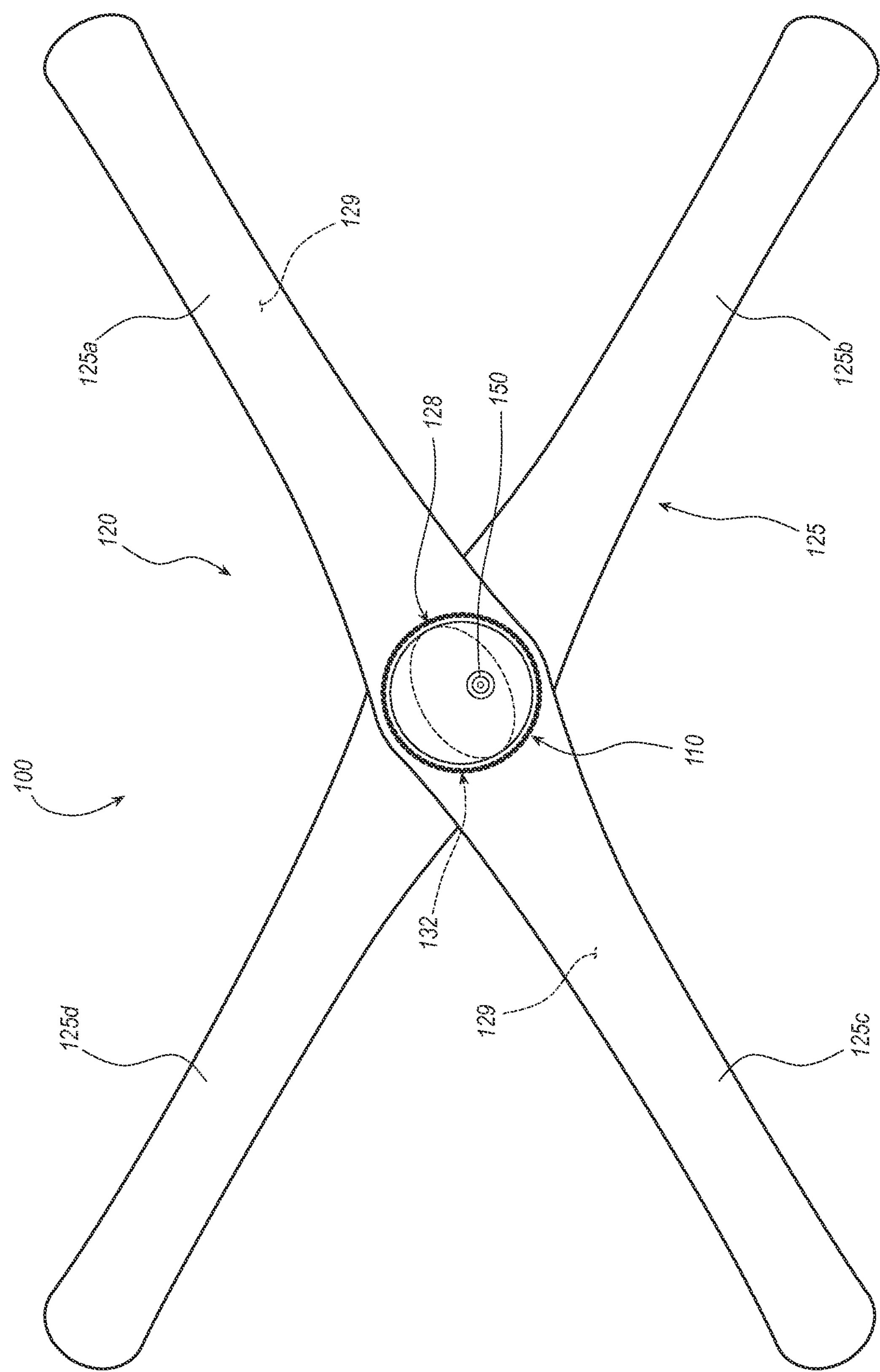
FIG. 3 is a top view of the compression device of FIG. 1 with the straps in a second configuration.
Figure 4:
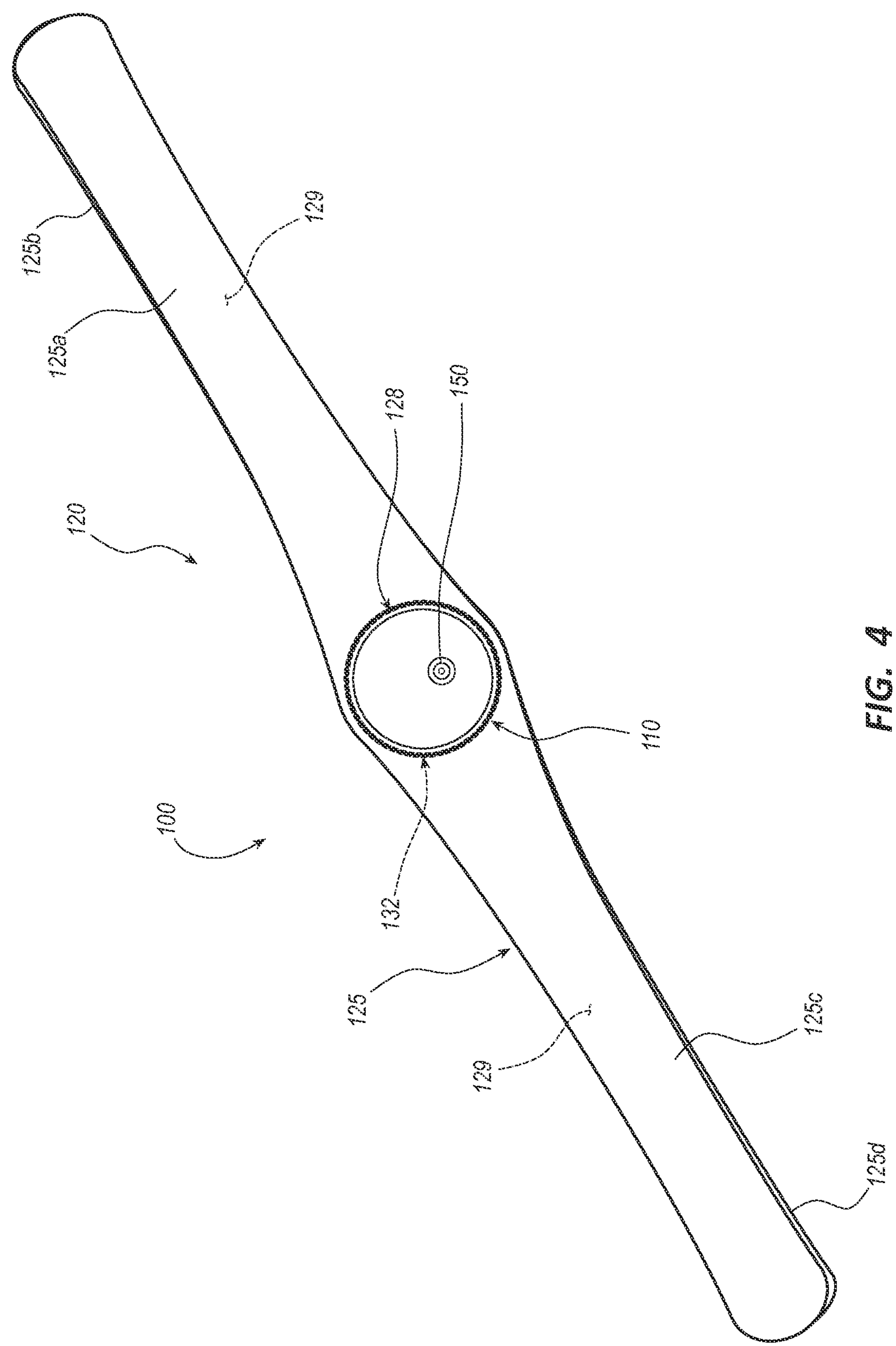
FIG. 4 is a top view of the compression device of FIG. 1 with the straps in a third configuration.

FIGS. 2-4 are top views of the compression device 100 of FIG. 1 illustrating three different strap configurations. As shown in FIG. 2, each strap 125 may comprise a free end and may be coupled to the compression member 110 at a fixed end. The straps 125 may be generally elongate in shape, i.e., having a greater longitudinal length than width. The width may vary along the length of the strap 125. For example, in the illustrated embodiment, the width is narrower in a middle portion and wider at both the free end and the fixed end of each strap 125. Other shapes and designs of the straps 125 are likewise within the scope of this disclosure. The width at the fixed end may be substantially equal to or greater than a cross-sectional dimension of the compression member 110, such as a diameter for example. While the straps 125 are shown as straight, straps 125 with curvature are also within the scope of this disclosure.

Though certain examples shown in the figures and described below may include four straps (such as the embodiment of FIGS. 1-4), embodiments with more or fewer straps are likewise within the scope of this disclosure. Disclosure given below with respect to any specific number of straps (such as four straps) may be analogously applied to embodiments with more or fewer straps, including two, three, four, five, six, and so on.

As shown in FIG. 2, the plurality of straps 125 are collectively referred to with the reference numeral 125, while the four individual straps of the illustrated embodiment are designated with reference numerals **125*a*, 125*b*, 125*c*, and 125*d*. Disclosure regarding the size, shape, design, or other structure of any individual strap of the plurality of straps 125 may be applied to any other individual strap. Each strap of the plurality of straps 125 may have the same length or the straps 125 may be of different lengths. In some embodiments, the length of one or more straps may be sufficient to extend around or partially around the torso of the patient 50. Embodiments wherein the straps 125 are shorter, for example, one, two, three, or four times a dimension of the compression member 110 (such as one, two, three, or four times the diameter of the compression member 110**) are likewise within the scope of this disclosure.

The straps 125 may comprise an adhesive 129 on an underside to facilitate attachment to the patient 50. The adhesive 129 may be distributed along the entire length and width of the straps 125. In some embodiments, a portion of the straps 125 may be free of adhesive such as a portion adjacent the free end so as to facilitate removal of the strap 125 from the patient 50 and/or a portion adjacent the fixed end so as to prevent adhesion to skin portions immediately adjacent the compression site 60. The adhesive 129 may be a pressure adhesive comprising a paper backing which upon removal enables the adhesive 129 for attachment of the strap 125 to the skin surface of the patient 50. In some embodiments, the straps 125 may be configured for the removal of portions of the backing paper while allowing other portions of the backing paper to remain. In such instances, a practitioner may selectively define attachment portions and non-attachment portions of the strap 125.

The straps 125 may be flexible so as to be conformable to the skin over or along uneven surface portions of the patient's body. The straps 125 may be stretchable or non-stretchable in one or more directions. The straps 125 may also comprise stretchable and non-stretchable portions. For example, a strap 125 may be non-stretchable adjacent the fixed end so that adhesion of the strap 125 to the skin surface may promote a downward force of the compression member 110. A strap 125 may be stretchable at locations disposed away from the compression member 110 so that discomfort of the patient may be minimized during movement of the patient 50. The straps 125 may comprise other locations of stretchable and non-stretchable portions along the length of the straps 125. Furthermore, some straps 125 may be more stretchable than other straps 125. In some embodiments, two or more straps 125 may be configured to provide compression support (downward force) to the compression member 110 while other straps 125 may be configured to laterally secure the location of the compression member 110 over the compression site 60. For example, two opposing straps 125, such as straps **125*a* and 125*c*, may be relatively long so as to extend at least partially around the torso of the patient 50**.

The two opposing straps 125 may also comprise enhanced flexibility so that tension in the straps 125 may be minimally affected by movement or contortion of the patient 50. The two opposing straps 125 may further comprise adhesive portions and adhesive free portions strategically located to facilitate tension in the straps 125 while minimizing discomfort to the patient 50. Straps 125 configured for lateral securement may be shorter and/or less stretchable and may be wider so as to extend along a portion of a circumference of compression member 110.

The plurality of straps 125 may be coupled to the compression member 110 such that each strap 125*a*, 125*b*, 125*c*, and 125*d* may pivot or rotate around the compression member 110. In other words, the straps 125 may be configured such that they may extend away from the compression member 110 at an adjustable direction or angle. In the illustrated embodiment, strap 125*a* and strap 125*c* are fixed with respect to each other as are strap 125*b* and strap 125*d*. That is strap 125*a* and strap 125*c* are constrained to be disposed at 180 degrees with respect to each other as are strap 125*b* and strap 125*d*. In some such embodiments, straps 125*a* and 125*c* may comprise one continuous member as may straps 125*b* and 125*d*. In such embodiments, changing the angle or direction of strap 125*a* with respect to the compression member 110 also changes the disposition of strap 125*c* and vice versa. In the illustrated embodiment, straps 125*b* and 125*d* also rotate about the compression member 110 together. In some embodiments, two or more straps 125 may be fixed with respect to each other at angles other than 180 degrees such as angles between 45 degrees and 180 degrees. In the illustrated embodiment, the straps 125*b* and 125*d* may be described as being on the bottom, i.e., disposed underneath straps 125*a* and 125*c*, and may be referred to herein as bottom straps 125. Similarly, the straps 125*a* and 125*c* may be described as being on the top, i.e., disposed on top of straps 125*b* and 125*d*, and may be referred to herein as top straps 125. Embodiments wherein each strap 125*a*, 125*b*, 125*c*, and 125*d* is independently rotatable about the compression member 110 are likewise within the scope of this disclosure as are embodiments wherein any subset of the straps 125, or the entire plurality of straps 125 are rotationally fixed with respect to the compression member 110. In one embodiment, the plurality of straps 125 may be fixed with respect to each other (that is the angles between the straps 125 are not adjustable) while the compression member 110 may rotate with respect to the plurality of straps 125.

The compression device 100 may comprise a plurality of ring members 128. Each strap 125 may be coupled to a ring member 128. The ring members 128 may be positioned at the fixed end of the strap 125 or the ring members 128 may be disposed away from the fixed end. In some embodiments, multiple straps may be coupled to the same ring member 128. For example, straps 125*a* and 125*c* may be formed of a single length of strap material and the ring member 128 may be disposed toward the center of the single length of strap material. In some embodiments, the strap 125 may be coupled to the ring member 128 along a partial circumference of the ring member 128 such as 50% or less of the total circumference of the ring member 128. In other embodiments, the strap 125 may be coupled to the ring member 128 along a larger portion of the circumference of the ring member 128 comprising 50 percent to 100 percent of the total circumference of the ring member 128. As such, the ring member 128 may comprise a portion of the strap 125. The strap 125 may be coupled to the ring member 128 using any suitable manufacturing technique. For example, the strap 126 may be bonded to the ring member 128 with adhesive or welding, such as ultra-sonic welding. The ring member 128 may also be insert molded to the strap 125. The ring member 128 may also comprise a slot through which a portion of the strap 125 may be looped. In some embodiments, the strap 125 may be attachable to and detachable from the ring member 128 by the practitioner. In some embodiments, the ring member 128 may be more rigid than the strap 125.

In some embodiments, ring members 128 may interface with the compression member 110 such that the ring member 128 may rotate with respect to the compression member 110 and/or with respect to other ring members 128. As such, the compression member 110 may define an axis of rotation about which one or more ring members 128 may rotate. Further, the compression member 110 may define a common axis of rotation about which all ring members 128 may rotate. Each ring member 128 may encircle or extend around the compression member 110 or at least a portion thereof. Each ring member 128 may be slidably coupled to the compression member 110 to facilitate rotation of the ring member 128 relative to the compression member 110.

In some embodiments, the compression member 110 may comprise an interface portion which may be circular (such as top plate 130 of FIG. 5) that is coupled or coupleable to each of the plurality of ring members 128. The interface portion and ring members 128 may be coupled such that the ring members 128 are allowed to rotate with respect to the interface portion. For example, in some embodiments, the compression member 110 may comprise one or more grooved portions 132 for engagement with mating portions of the ring members 128 to facilitate relative rotation. Embodiments wherein the straps 125 are coupled to slots in the compression member 110 or coupled to shuttles or other intermediate members that are displaceable with respect to the compression member 110 are likewise within the scope of this disclosure. In some such embodiments, the compression member 110 need not have a circular shape, and shuttles may be displaceable along any shape or design, including straight edges and/or curves. Disclosure herein relating to "rotating" the straps 125 or ring member 128 may thus also be analogously applied to displacement of shuttles, displacement of straps 125 along a slot, or any other arrangement wherein the straps 125 can be displaced with respect to the compression member 110, including displacement along a perimeter of the compression member 110.

Embodiments wherein the ring members 128 are configured such that they are attachable to and detachable from the compression member 110 by a practitioner are within the scope of this disclosure as are embodiments wherein the ring members 128 may be rotated by a practitioner but are not configured to be completely detached from the compression member 110 by a practitioner. In embodiments wherein the ring members 128 are non-detachable from the compression member 110, the straps 125 may likewise be configured as non-detachable from the compression member 110 by a practitioner. Embodiments wherein any number of the straps 125 and the associated ring members 128 are detachable from and/or attachable to the compression member 110 by a practitioner are likewise within the scope of this disclosure. In some instances, a practitioner may determine that one or more straps 125 are not necessary for the application and detach one or more straps from the compression member 110. In other instances, a practitioner may determine that one or more additional straps 125 are necessary for the application and attach one or more straps 125 to the compression member 110.

Each ring member 128, and therefore each strap 125, may provide a viewing window 133 facilitating visual observation of the compression site 60 and/or the compression member 110. Thus, the ring members 128 may be configured to facilitate placement of the compression member 110 at the compression site 60 by allowing direct viewing of the compression member 110 together with the compression site 60 by a practitioner during use. In some instances, the compression site 60 may comprise an elongate puncture site or incision of the skin and therefore, the ring members 128 may also be configured to facilitate rotational alignment of the compression member 110 with the elongate puncture site by allowing direct viewing of the compression member 110 together with the compression site 60 by a practitioner during use.

As detailed above, the plurality of ring members 128 may be configured to allow the plurality of straps 125 to rotate with respect to the compression member 110. As also noted above, embodiments wherein each strap 125 of the plurality of straps 125 may rotate with respect to the compression member 110 are within the scope of this disclosure as are embodiments wherein any number of the straps 125 are fixed with respect to the compression member 110 and/or other straps 125. Embodiments wherein any number of the straps 125 are directly coupled to the compression member 110 are also within the scope of this disclosure, including embodiments wherein such straps 125 are rotationally fixed with respect to the compression member 110.

Two or more straps 125 may be coupled together at their fixed ends such that the two or more straps 125 share a common ring member 128. For example, and as noted above, in the illustrated embodiment, the compression device 100 comprises two pairs of straps: straps 125*a*, 124*c* defining one pair and straps 125*b*, 125*d* defining another pair. Pairs of straps (such as straps 125*a*, 125*c* and/or straps 125*b*, 125*d*) may share a common ring member 128 and thus the pairs of straps may be rotationally fixed with respect to each other. Any one pair of straps 125 may be configured to be rotated with respect to any other pair of straps 125 and/or with respect to the compression member 110.

In the illustrated embodiment, the compression device 100 comprises one ring member 128. In that embodiment, straps 125*a* and 125*c* are coupled directly to the compression member 110 and do not rotate with respect to each other or with respect to the compression member 110. The ring member 128 is coupled to the compression member 110 such that the ring member 128 may rotate with respect to the compression member 110 and straps 125*b* and 125*d* are coupled to the ring member 128 such that they are fixed with respect to the ring member 128 and rotate together with the ring member 128. Thus, in the illustrated embodiment, the angles between the pairs of straps 125 may be adjusted through rotation of the ring member 128.

FIG. 2 shows the pairs of straps 125 in a first configuration where the pairs are disposed at an angle of approximately 90 degrees relative to each other. Stated one way, the angle between strap 125*a* and strap 125*b* is approximately a 90-degree angle. The configuration of FIG. 3 shows the pairs or straps having been rotated with respect to the configuration shown in FIG. 2. That is, as compared to FIG. 1, in the configuration of FIG. 3, the ring member 128 has been rotated with respect to the compression member 110 such that the angle between strap 125*a* and strap 125*b* is less than 90 degrees. In the configuration of FIG. 4, the ring member 128 has been rotated such that strap 125*b* is disposed directly under strap 125*a*, thus these straps overlap each other and are disposed at a zero angle with respect to each other.

Comparison of FIGS. 2-4 illustrates how the compression device 100 may be configured to adjustably allow a practitioner to attach the compression device 100 to a patient 50. The practitioner may adjust the ring member 128 (and thus the relative positions of the straps 125) in order to accommodate the patient's anatomy and the position of the pocket or other compression site 60. That is, prior to formation of the pocket, a practitioner may not know the best angle for disposition of the straps 125 with respect to the compression member 110. However, the ability to rotationally displace one or more straps 125 may allow the practitioner to position the compression member 110 at a desired location and orientation with respect to the compression site 60, while adjusting one or more straps 125 to place the straps 125 at a desired position. In some specific instances, it may be desired to pass one strap 125 over the shoulder near the neck and the other strap over or toward the other shoulder on the other side of the neck. In some instances, a strap may be extended toward a sternum area of the patient as the sternum area may comprise skin that is less susceptible to lateral movement when tension is applied to the strap 125. Adjustability of the straps 125 thus allows for variations in pocket location, patient size, patient anatomy, and so forth while facilitating desired placement of the straps 125.

In use of the illustrated embodiment, one exemplary procedure may include first placing the compression member 110 on the patient 50 in a specific or desired orientation with respect to the compression site 60. (As described below, in some instances the compression site 60 may be elongated or wider that it is tall, thus, in some instances an elongate shaped compression member 110 may be positioned to align with the elongate compression site 60.) Once the orientation and position of the compression member 110 are determined, a practitioner may adjust the rotational position of straps 125*b* and 125*d* with respect to the compression member 110 in order to position the straps 125 in a desired position on the patient 50. The practitioner may then remove adhesive backing from the straps 125 and adhere the straps 125 to the patient 50. In some therapies, the practitioner may adhere the bottom straps 125*b* and 125*d* to the patient 50 first, then adhere the top straps 125*a* and 125*c*. This exemplary procedure may be modified for embodiments wherein the straps that are configured to rotate with respect to the compression member 110 comprise the top straps rather than the bottom straps, embodiments wherein all of the straps 125 may rotate with respect to the compression member 110, embodiments wherein all the straps 125 are rotationally fixed with respect to each other and the compression member 110 can rotate with respect to the straps 125, and so forth.

The order of positioning the compression member 110 positioning any of the straps 125, and/or removing adhesive backing from any of the straps, may be modified depending on practitioner preference, compression site location, compression device design and configuration, and so forth. In some instances, the compression member 110 may be first located over the compression site 60 and then each strap 125 may be tensioned and attached to the skin surface to maximize tension in the straps 125. For example, after initially locating the compression member 110, the practitioner may pull on strap 125*a* so as to establish tension in the strap 125*a* and attach the strap 125*a* to the skin. In this instance, the tension in the strap 125*a* may temporarily dislocate the compression member 110 toward the strap 125*a* away from the compression site 60. The practitioner may then pull on strap 125*c* in the direction opposite to strap 125*a* so as to establish tension in the strap 125*c* which may temporarily dislocate the compression member 110 toward the strap 125*c* away from the compression site 60 and attach the strap 125*c*. Once strap 125*c* is attached to the skin, the skin may stretch adjacent to strap 125*c* so as to allow the tension in strap 125*a* to reposition the compression member over the compression site 60. In this way, the skin may be pre-stressed or pre-tensioned prior to inflating the bladder 140, and therefore, provide an enhanced resistance to upward movement of the compression member 110 upon inflation of the bladder 140. The process of tensioning and attaching of straps 125*a* and 125*c* may be applied to straps 125*b* and 125*d* to further enhance resistance to upward movement of the compression member 110 upon inflation of the bladder 140. In some instances, the pre-stress of the skin as established by straps 125*a* and 125*c* may facilitate a greater tension to be established in straps 125*b* and 125*d*. Hence, the tension in the straps 125*b* and 125*d* may be different, and may be greater, than the tension in the straps 125*a* and 125*c*.

Embodiments wherein one set of straps (such as 125*a* and 125*c*) are fixed to the compression member 110 and a second set of straps (such as 125*b* and 125*d*) are a separate component are also within the scope of this disclosure. In such embodiments, the fixed straps may be positioned and attached to the patient 50, and the second set disposed over the first set, where the second set has an opening to surround the compression member 110 with a ring or collar surrounding the opening configured to engage the compression member 110 so as to provide downward force on the compression member 110 when the second set is tensioned and attached to the patient 50.

In some embodiments, the securement system 120 may comprise one or more straps 125 configured to wrap around a portion of the patient 50 and attach to itself or each other. In such embodiments, the straps 125 may comprise any suitable releasable securement mechanism, such as a hook-and-loop fastening mechanism, pressure sensitive adhesives, buckles, magnets, snaps, clasps, etc., all of which are contemplated to be within the scope of this disclosure.

Rotational displacement of the plurality of straps 125 may be configured to facilitate storage or shipping of the compression device 100. For example, when disposed in the configuration of FIG. 4, the compression device may be configured to be placed in a package (without rolling or folding the straps 125) with smaller dimensions or a more efficient shape than a package configured to receive the compression device 100 with four fixed straps 125 extending at angles relative to each other. Thus, one or more rotational positions of the straps 125 may correlate to a storage or shipping configuration. Embodiments wherein four or more (or any number of) straps 125 may all be rotated, and all overlap, are also within the scope of this disclosure.

The compression member 110 may be configured to provide compression over a specifically defined area of a patient 50. The compression member 110 may comprise a symmetrical or non-symmetrical shape. The shape may be configured to correlate with the anatomy of a patient 50 adjacent a compression site 60. The shape may also facilitate proper alignment and placement of the compression device 100. The compression member 110 may comprise a window 133 through which the practitioner may observe the compression site 60 as further described below.

FIGS. 5-8B illustrate various views of the compression member 110 of the compression device 100 of FIGS. 1-3. The straps (125 of FIG. 1) and ring members (128 of FIG. 1) are not shown in FIGS. 5-8B. Features of the compression member 110 described below may be used with disclosure described above detailing the straps (125 of FIG. 1) and other features described in connection with FIGS. 1-4. Additionally, certain properties, features, and characteristics described herein may also apply to compression devices configured to provide compression to any location on a patient 50 and for any therapy where compression is beneficial, including embodiments with any subset of the elements and features of the embodiment shown in the figures.

Figure 5:
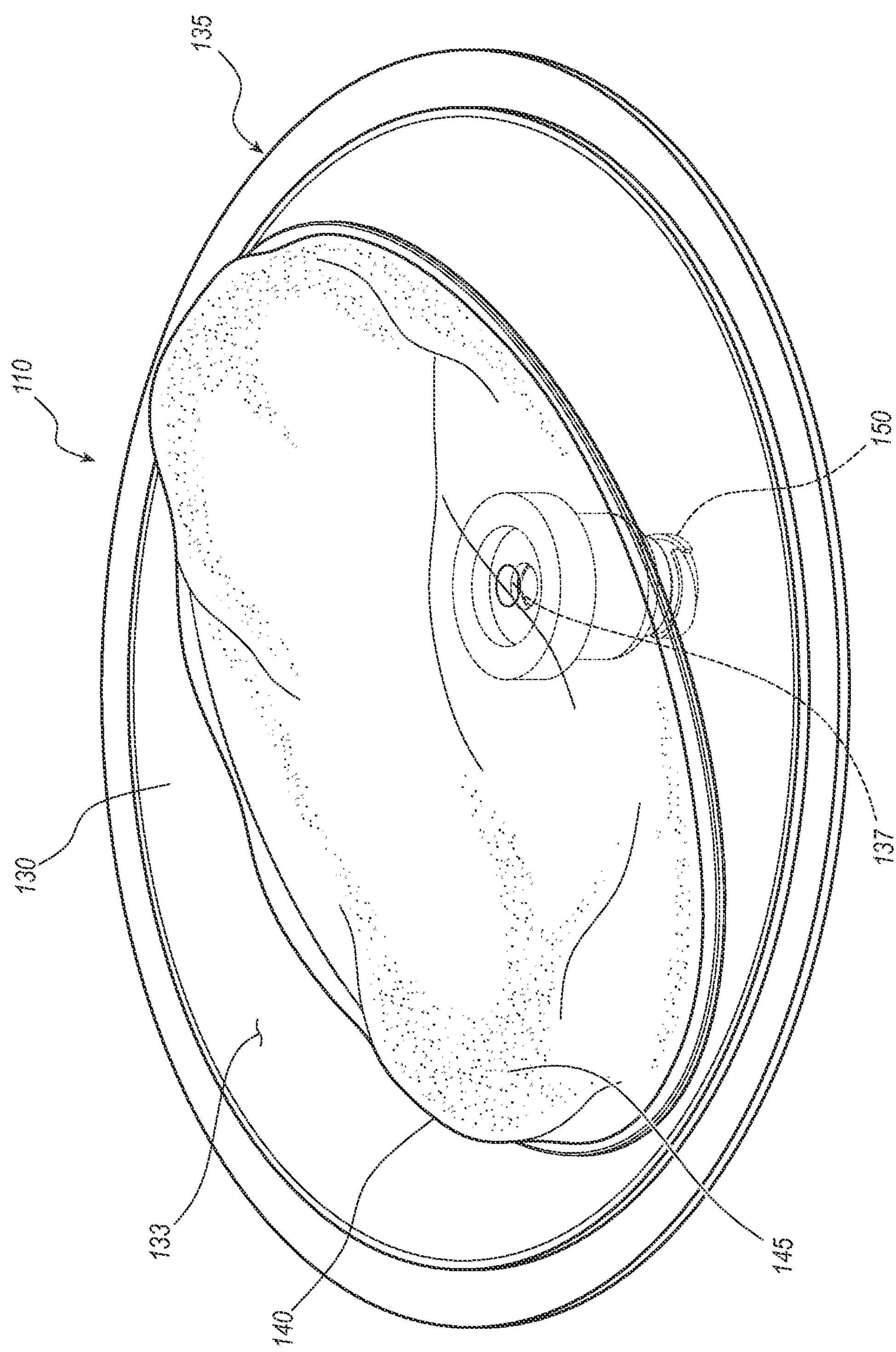
FIG. 5 is a bottom view of a compression member of the compression device of FIG. 1.
Figure 6B:
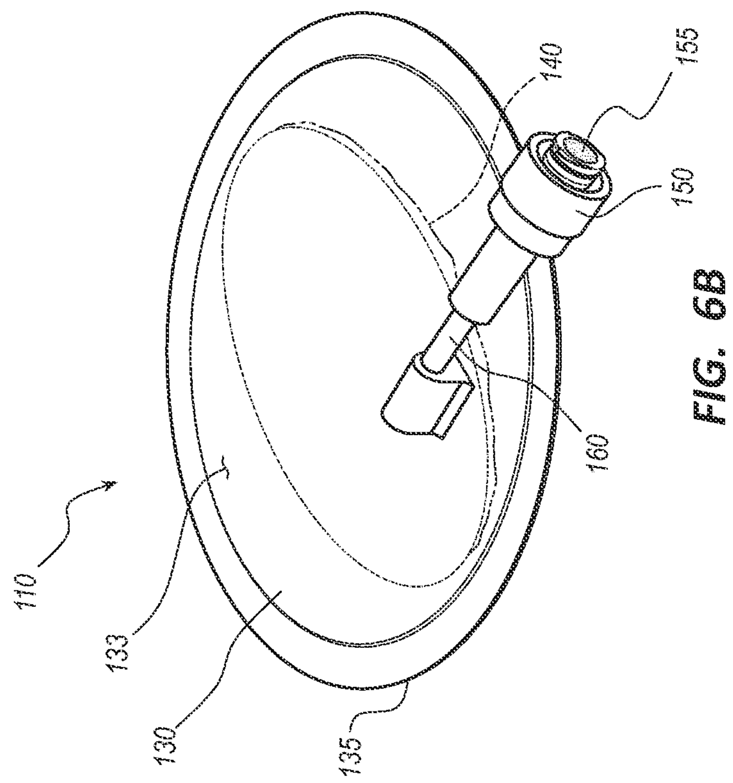
FIG. 6B is a top view of an alternative embodiment of the compression member of FIG. 5.
Figure 6A:
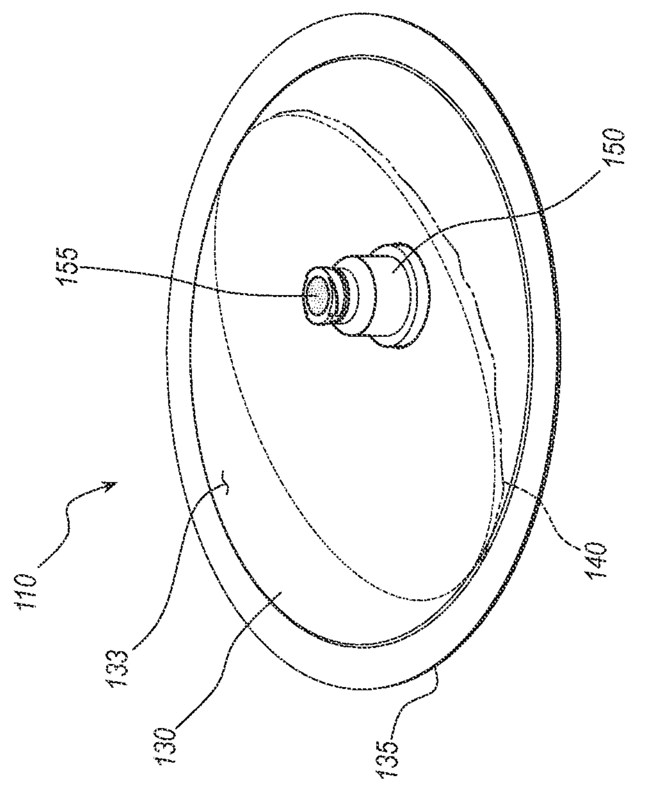
FIG. 6A is a top view of the compression member of FIG. 5.

As shown in FIGS. 5 and 6A, the compression member 110 may comprise a top plate 130, a bladder 140, and an inflation port 150. FIG. 5 is a bottom view of the compression member 110 and FIG. 6A is a top view of the compression member 110. The bladder 140 may be disposed on the bottom or underside of the compression member 110 so as to be disposed adjacent the skin of a patient 50. The bladder 140 may be configured to provide compression to a compression site 60 when the bladder 140 is at least partially inflated. The bladder 140 may be coupled to the top plate 130 and may be in fluid communication with the inflation port 150 via an orifice 137.

The top plate 130 may be configured to convert attachment of the securement system (120 of FIG. 1) to the skin surface of the patient 50 into a downward force of the compression member 110 on the patient 50. The top plate 130 may be shaped such that attachment of one or more straps (125 of FIG. 1) to the skin surface of the patient 50 may facilitate a downward force of the compression member 110 and/or may prevent the displacement of the compression member 110 away from the patient 50 when the bladder 140 is inflated. Similarly, the top plate 130 may be shaped so that tension in one or more straps (125 of FIG. 1) may further facilitate the downward force of the compression member 110.

The top plate 130 may be configured to provide a support for the bladder 140. The top plate 130 may be rigid. The top plate 130 may also be semi-flexible or flexible so as to conform to the anatomy of a patient 50 upon securement and/or flex as the bladder is inflated. The top plate 130 may comprise a substantially flat plate, and/or may comprise flat, curved, convex, or concave portions. Further, the top plate 130 may be symmetrical or non-symmetrical. In the illustrated embodiment, the top plate 130 may facilitate coupling of the securement system (120 of FIG. 1) to the compression member 110. In the illustrated embodiment, the top plate 130 comprises a perimeter 135 which may be circular. In other embodiments, the top plate may be oval or polygonal having a plurality of sides, such as rectangular for example. The sides may be straight, concave or convex.

Figure 7:
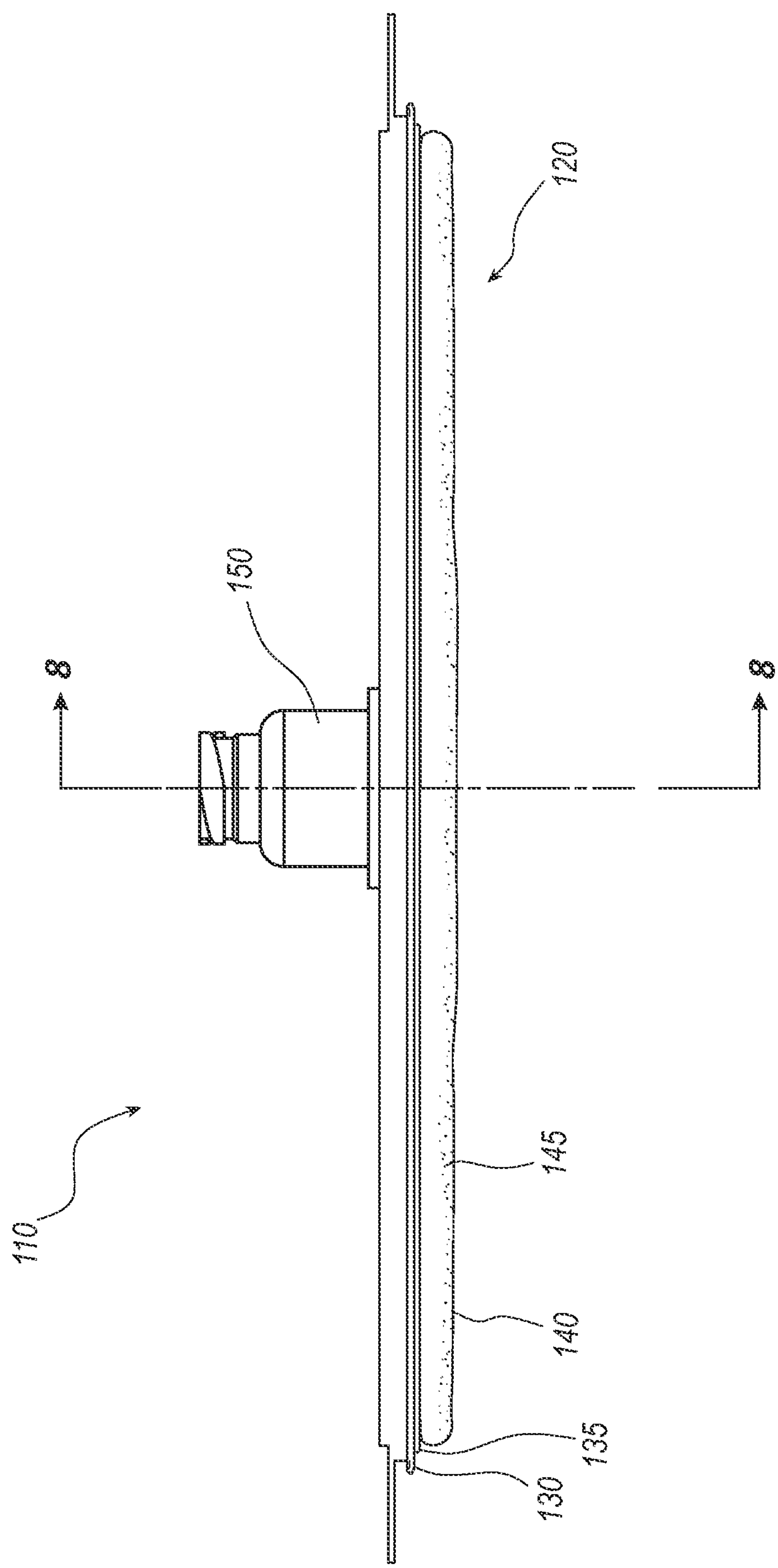
FIG. 7 is a side view of the compression member of FIG. 5.
Figure 8A:
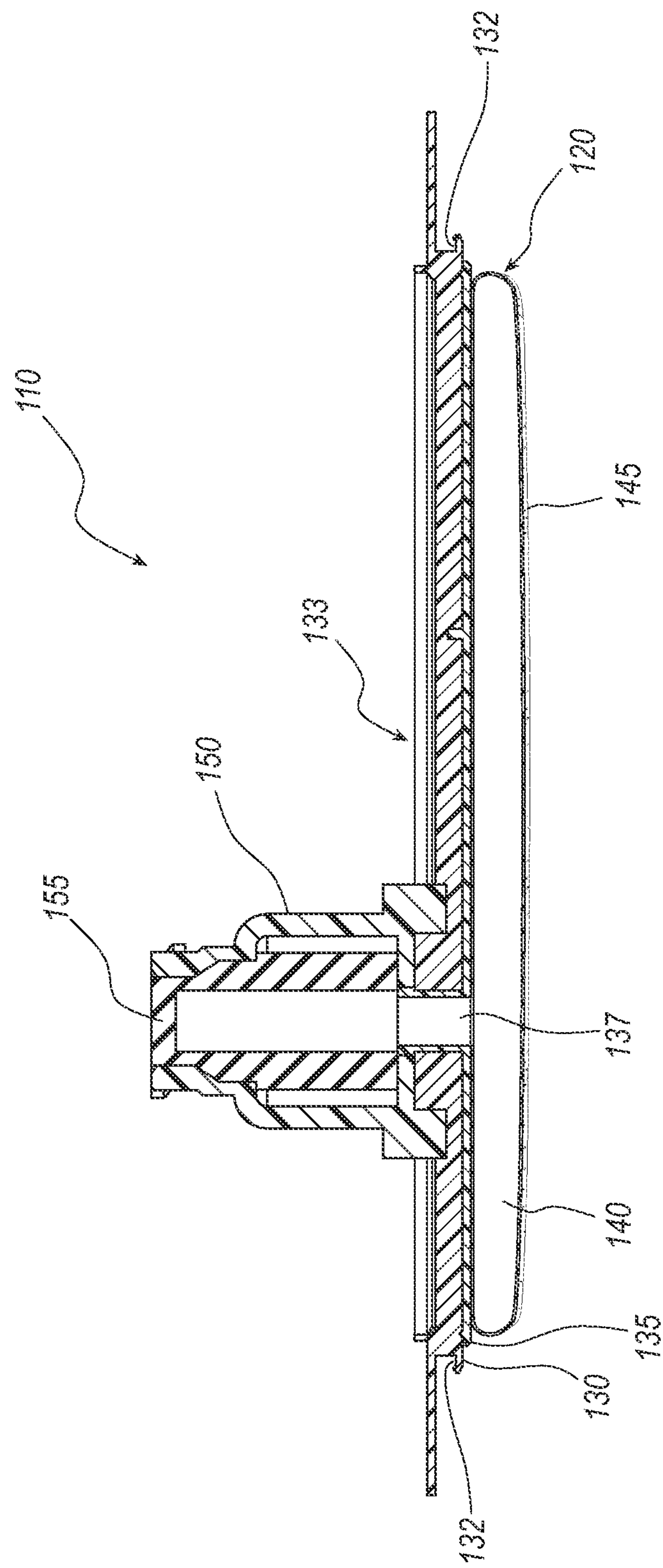
FIG. 8A is a cross-sectional side view of the compression member of FIG. 5 cut along sectioning lines 8-8 with the bladder in an uninflated state.
Figure 8B:
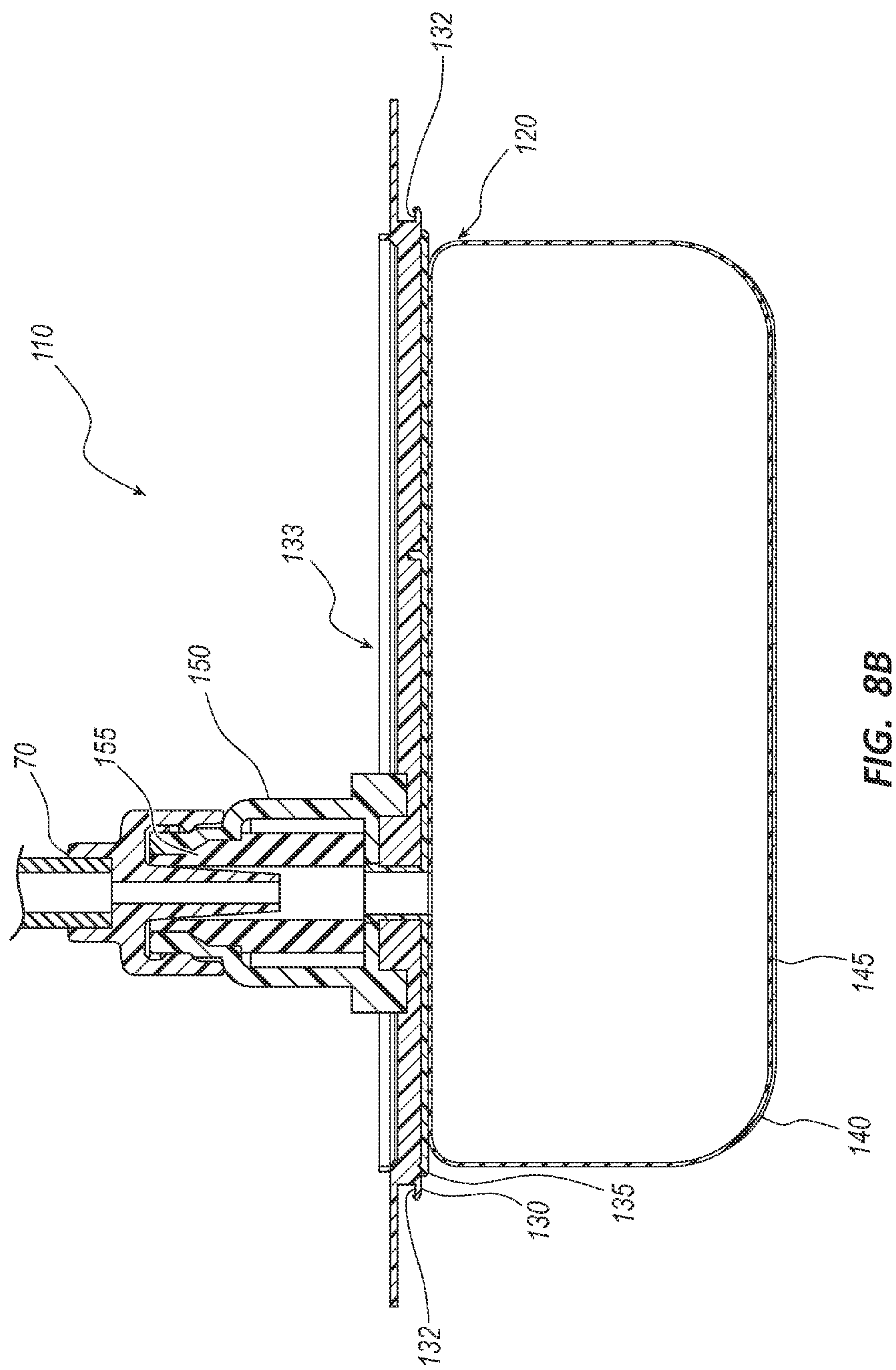
FIG. 8B is a cross-sectional side view of the compression member of FIG. 5 cut along sectioning lines 8-8 with the bladder in an inflated state.

With reference to FIGS. 7-8B, the perimeter 135 may be configured to facilitate coupling of the securement system 120 to the top plate 130. In some embodiments, the top plate 130 may comprise one or more grooved portions 132 sized and shaped to engage the ring members 128. The one or more grooved portions 132 may constrain lateral displacement of the ring members 128 relative to the top plate 130. In some embodiments, the one or more grooved portions 132 may be a single external annular groove extending entirely around a circular perimeter of the top plate 130. In other embodiments, the one or more grooved portions 132 may comprise two or more grooved portions 132 disposed on the top plate 130. The one or more grooved portions 132 may be sized to accommodate 1 or more ring members 128. In other embodiments, the one or more grooved portions 132 may be sized to accommodate 2 or more ring members 128 in a stacked configuration within a single groove. The one or more grooved portions 132 may also comprise multiple grooves, each sized to a single ring member 128. As also noted above, embodiments wherein the perimeter 135 is non-circular and/or wherein the straps 125 are displaceable along grooves, via interaction with shuttles, and so forth are also within the scope of this disclosure.

The top plate 130 may be configured to be anatomically compatible with a patient 50, such as avoiding uncomfortable contact points. The top plate 130 may also be configured to provide some level of compression without inflation of the bladder 140 such as comprising a convex portion on the bottom side thereof.

A bottom surface of the top plate 130 may comprise features such as protrusions, surface displacements, variations in thickness, position or alignment indicators, surface texturing, etc. to facilitate welding or bonding of the bladder 140 to the top plate 130. A top surface of the top plate 130 may also comprise features such as protrusions, surface displacements, variations in thickness, position or alignment indicators, surface texturing, etc. to facilitate welding or bonding of the inflation port 150 to the top plate 130. The top plate 130 may comprise an orifice 137 extending through the top plate 130 to establish fluid communication from the inflation port 150 to the bladder 140.

The top plate 130 may be transparent or translucent so as to define a window 133, so that the compression site 60 and/or the bladder 140 may be visually observed through the top plate 130. Such visual observation may facilitate alignment of the compression member 110 with the compression site 60 and assessment of hemostasis during treatment. The top plate 130 may be formed of any suitable flexible or semi-flexible material such as polyethylene, polypropylene, polyvinyl chloride, polyurethane, etc. or any suitable rigid material, such as polycarbonate, polystyrene, styrene copolymers, polyethylene terephthalate, acrylic, polyethylene, polypropylene, etc.

FIG. 6B illustrates an alternative embodiment of the compression member 110. In this embodiment, the inflation port 150 is coupled to the top plate 130 via a tube 160. The tube 160 provides fluid communication between the inflation port 150 and the orifice 137 of the top plate 130 and the bladder 140. The tube 160 may be coupled to the top plate 130 such that the tube 160 extends along the surface of the top plate 230 or in other words the tube 160 may be disposed parallel to the top plate 130. The tube 160 may also be coupled to the top plate 130 such that the tube 160 is oriented toward a specified direction such as toward an opening in the patent's clothing and the tube 160 may be of sufficient length to extend through an opening in the patient's clothing. As such, the inflation port 150 may be disposed away from the top plate 130 and in a position of greater convenience for the practitioner. Such an embodiment may facilitate inflation and deflation of the bladder 140 while the compression member 110 is covered by bandages or clothing for example. Such an embodiment may also facilitate inflation and deflation of the bladder 140 when the patient 50 is disposed in a position such that the compression member 110 is not directly accessible and thus would require repositioning of the patient 50 to provide access to the inflation port 150.

FIGS. 7-8B illustrate various side views of the compression member 110. FIG. 7 is a side view of the compression device 100 with the bladder 140 in an uninflated state and FIGS. 8A and 8B are cross-sectional side views cut along sectioning lines 8-8 of the compression member 110 with the bladder 140 in an uninflated state and an inflated state, respectively. The bladder 140 may be configured to extend downward from the top plate 130 upon inflation. The bladder 140 may be disposed on the bottom surface of the top plate 130 such that the top plate 130 limits or controls upward expansion of the bladder 140. The bladder 140 may be configured to be in contact with a patient's skin and provide compression to the compression site 60. The bladder 140 may be configured to be inflatable and deflatable, by the passage of fluid through the inflation port 150. Displacement of fluid into or out of the bladder 140 may thus inflate or deflate the bladder 140. Thus, the bladder 140 may be configured to contain an inflation fluid, including a pressurized inflation fluid, over a period of time, such as the desired time of compression of a compression site 60. In some embodiments, an internal fluid pressure within the bladder 140 may correlate to the compressive pressure or level of compression applied to a patient 50. The bladder 140 may be configured to provide the desired compression while only partially inflated.

The shape of the bladder 140 may be configured to provide compression to a compression site 60 over a predefined area or shape, including elongate shapes or areas. For example, the bladder 140 may be configured to provide a predefined compression depth profile. In some circumstances, the compression area on a patient 50 may be relatively large or small and the compression profile may be relatively deep or shallow defining a range of volumetric capacities for the bladder 140.

The bladder 140 may comprise a flat sheet or a pre-formed three-dimensional shape. The bladder 140 may be flexible and non-stretchable or flexible and stretchable. The bladder 140 may be transparent or translucent to facilitate visible observation of a compression site 60 through the window 133.

The bladder 140 may be coupled to the top plate 130 such that the top plate 130 defines one boundary of the bladder 140 when inflated, or the bladder 140 material may extend around an entire inflatable volume and the bladder 140 be coupled to the top plate 130. In some embodiments, the bladder 140 may be sealably coupled to the top plate 130 along a perimeter of the bladder 140 such that a portion of the top plate 130 forms a top wall of the bladder 140. The orifice 137 may be disposed within the perimeter of the bladder 140, including extending through a bladder 140 membrane and/or extending through the top plate 130 and thus accessing the interior of the bladder 140.

The bladder 140 may be configured to define specific compression characteristics. Such characteristics may comprise the area, depth, and shape of the compression on a patient 50. The bladder 140 of the illustrated embodiment, as seen in FIGS. 4 and 5, comprises an oval shape. Various shapes and configurations are within the scope of this disclosure, including ovals, rectangles, rectangles with curved corners, partial rectangles with curved minor ends, and so forth.

In some embodiments, a hemostasis enhancement substance 145 may be applied to an external surface of the bladder 140 so that upon placement of the compression device 100, the hemostasis enhancement substance 145 may contact an area of the patient's skin comprising the compression site 60 and thereby provide an enhanced hemostatic effect. In some embodiments, the hemostasis enhancement substance 145 may comprise a sugar that is obtained from the hard outer skeleton of shellfish, including crab, lobster, and shrimp, for example Chitosan. It has been shown that Chitosan when topically applied is helpful to stop bleeding after surgeries. Other hemostasis enhancement substances 145 are also included within this disclosure. In some embodiments, the hemostasis enhancement substance 145 may be provided in a solid form such as a powder which is attached to the outside surface of the bladder 140. The hemostasis enhancement substance 145 may in some instances interfere with or otherwise reduce the transparency of the bladder 140. As such, the amount of hemostasis enhancement substance 145 applied to the bladder 140 may be limited or controlled in a manner so as to provide the enhanced hemostatic effect while minimizing any reduction in visibility through the bladder 140.

FIG. 8B shows a cross-sectional side view of the compression member 110 illustrating a compression profile of the bladder 140. As illustrated, the bladder 140, when inflated, defines a compression profile or volumetric shape when the bladder 140 is inflated. In the illustrated embodiment, the bottom of the bladder 140 may comprise minimal curvature, meaning a generally flat profile along the area configured to contact the compression site 60. Embodiments wherein the bladder 140 comprises a round profile or other profiles having an apex are likewise within the scope of this disclosure. In some instances, the bladder 140 may comprise a polymeric membrane thermoformed or otherwise set in a particular shape or profile. In the illustrated embodiment, the bladder 140 may be configured such that the sides of the bladder collapse in an "accordion" fashion as the bladder is deflated and the bottom compression surface of the bladder retains a generally flat configuration.

The profile of the bladder may also be related to or affected by one or characteristics of the bladder 140. Such characteristics may comprise thickness variation and/or a three-dimensional shape. The bladder 140 may comprise a thick portion on the bottom to facilitate a relatively flat or uniform compression area on the compression site 60. The bladder 140 may comprise pre-formed folds, such as a bellows arrangement, to facilitate a predefined compression depth and/or profile and to facilitate the "accordion" manner in which the sides may collapse as the bladder 140 is deflated. The pre-form of the bladder 140 may also define a perimeter bonding area of the bladder 140. The bladder 140 may be formed from any suitable, flexible, transparent or translucent material, such as polyethylene, polypropylene, polyurethane, etc.

The inflation port 150 may be in fluid communication with the bladder 140. The inflation port 150 may be coupled to the top plate 130 such that the inflation port 150 is in fluid communication with the orifice 137. As such, fluid communication between the inflation port 150 and the bladder 140 may comprise the orifice 137. The inflation port 150 may be disposed toward an outer perimeter of the bladder 140 such that the inflation port 150 does not obstruct visualization of the compression site 60. FIGS. 5, 6A, and 7-8B show the inflation port 150 oriented perpendicular to the top plate 130. However, the inflation port 150 may be coupled at any angle relative to an axis perpendicular to the top plate 130. Methods of coupling the inflation port 150 to the top surface of the top plate 130 and the bladder 140 to the bottom surface of the top plate 130 may comprise ultra-sonic welding, radio frequency welding, solvent bonding, boding with adhesives, etc. The inflation port 150 may be configured to be releasably coupleable to an inflation device 70, such as a syringe for example.

The inflation port 150 may comprise a valve 155 to facilitate inflation and deflation of the bladder 140 and containment of fluid within the bladder 140. The valve 155 may be configured to open and thereby allow fluid to flow through the inflation port 150 in direct response to coupling the inflation port 150 to the inflation device 70. In similar fashion the valve 155 may be configured to close and prevent or minimize flow through the inflation port 150 in direct response to decoupling the inflation port 150 from the inflation device 70.

The manufacturing process of the compression member 110 may comprise coupling the inflation port 150 and the bladder 140 to the top plate 130. The manufacturing process may also comprise adding or removing fluid from the bladder 140 after coupling the bladder 140 and the inflation port 150 to the top plate 130. The manufacturing process of the compression device 100 may further comprise coupling the compression member 110 to a securement system 120 and adjusting the disposition of the straps 125 of the securement system 120, including in an aligned configuration as shown in FIG. 4. Such an aligned configuration may facilitate placement of the compression device 100 within a package having a desirable shape for shipping and or storage.

Various methods of use and treatment are within the scope of this disclosure. While certain examples of methods of treatment are described herein, methods within the scope of this disclosure include any subset of the steps recited and re-ordering of the steps as described.

During some therapies, the bladder 140 may be initially uninflated, partially inflated, or substantially fully inflated, or the bladder 140 may initially contain a vacuum. The practitioner may adjust the level of inflation of the bladder 140 prior to placing the compression member 110 on the patient 50. For example, the practitioner may partially inflate the bladder 140 so that compression may be applied to the compression site 60 while the securement system 130 is being attached to the patient 50. The practitioner may rotationally align the compression member 110 with one or more portions of the patient 50 such as an artery, a vein, an incision of the skin, a bone, a pocket, or an anatomical recess, for example.

The practitioner may secure the compression member to the patient using the securement system. The practitioner may rotate at least a first pair of straps relative to the compression member and align the first pair in an orientation to facilitate positional stability of the compression member in one or more directions. The practitioner may enable the adhesive, e.g., remove a backing paper to expose the adhesive, of the first pair of straps, and attach the first pair of straps to the skin surface of the patient. The first pair of straps may be the bottom pair of straps disposed immediately adjacent the patient, i.e., between the patient and a second pair of straps. The practitioner may rotate the second pair of straps relative to the compression member and align the second pair in an orientation to facilitate additional positional stability of the compression member in one or more other directions. The practitioner may adjust tension in the straps to facilitate a downward force of the compression member and/or facilitate comfort of the patient. The practitioner may enable the adhesive (remove the backing paper) of the second pair of straps and attach the second pair of straps to the skin surface of the patient.

The practitioner may fluidly couple an inflation device to the inflation port thereby opening the valve. The practitioner may adjust the level of inflation in the bladder after securement so as to prevent, minimize, or control bleeding at the compression site. The practitioner may visually observe the compression site through the window and adjust the level of inflation in the bladder in response to visual observation made through the window. The practitioner may adjust the level of inflation of the bladder according to a predetermined protocol or in response to a patient condition such as discomfort, bleeding, etc. The practitioner may disconnect the inflation device from the inflation port thereby closing the valve. Once hemostasis is achieved, and/or sufficient healing has taken place, the securement system may be separated from the skin of the patient and the compression member removed.

Figure 9:
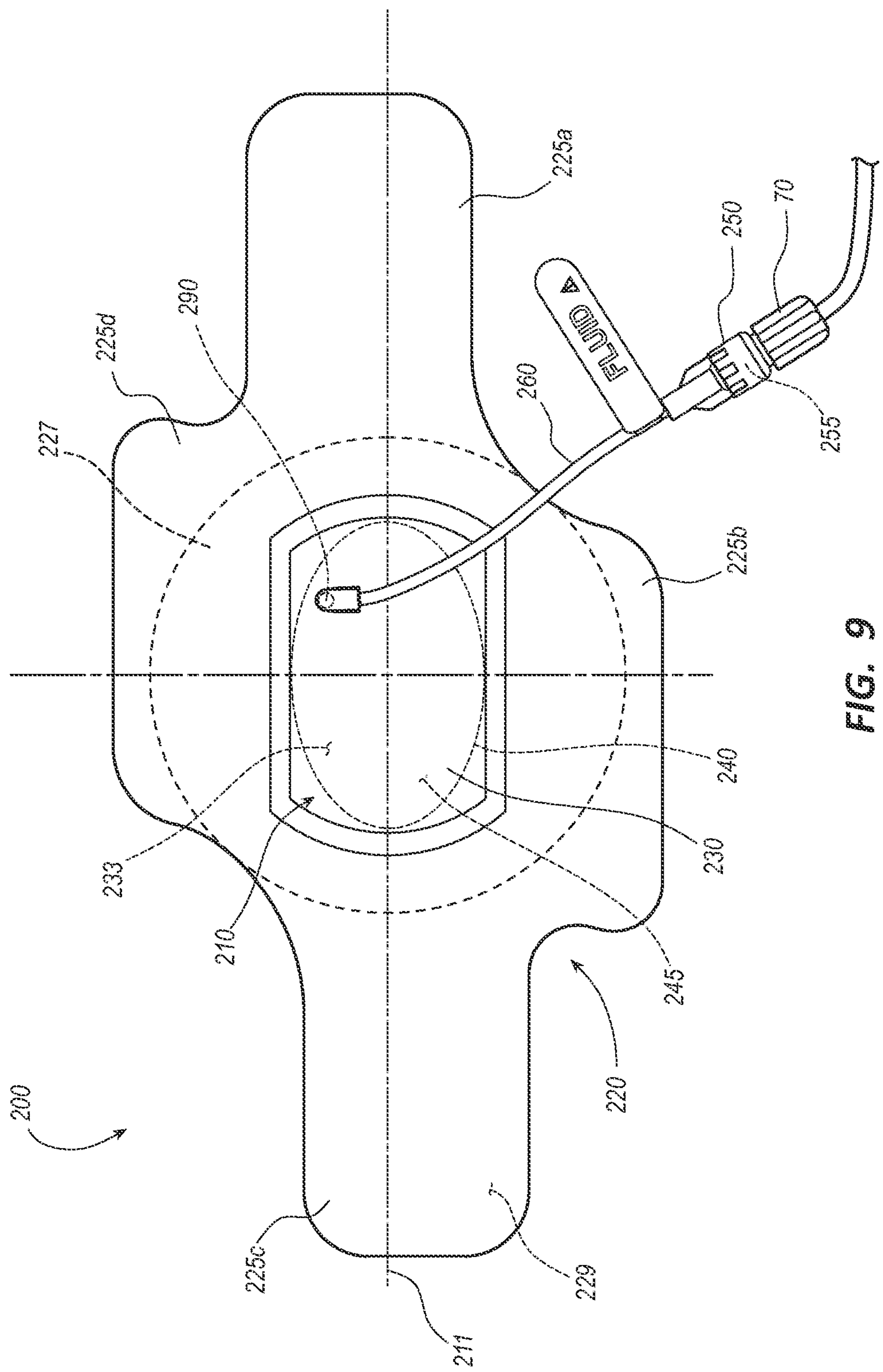
FIG. 9 is a top view of another embodiment of an inflatable compression device.

FIG. 9 depicts an embodiment of an inflatable compression device 200 that resembles the compression device 100 described above in certain respects. Accordingly, like features and/or components are designated with like reference numerals, with the leading digits incremented to "2." For example, the embodiment depicted in FIG. 9 includes a compression member 210 that may, in some respects, resemble the compression member 110 of FIGS. 1-8B. Relevant disclosure set forth above regarding similarly identified features and/or components thus may not be repeated hereafter. Moreover, specific features of the compression device 100 shown in FIGS. 1-8B may not be shown or identified by a reference numeral in the drawings or specifically discussed in the written description that follows. However, such features and/or components may clearly be the same, or substantially the same, as features depicted in other embodiments and/or described with respect to such embodiments. Accordingly, the relevant descriptions of such features and/or components apply equally to the features of the compression device 200 and related components depicted in FIG. 9. Any suitable combination of the features, and variations of the same, described with respect to the compression device 100 and related components as illustrated in FIGS. 1-8B can be employed with the compression device 200 and related components of FIG. 9, and vice versa. This pattern of disclosure applies equally to further embodiments depicted in subsequent figures and described hereafter, wherein the leading digits may be further incremented.

FIG. 9 is top view of an inflatable compression device 200. The compression device 200 may be configured to provide a variable compressive pressure or level of compression to a compression site 60. The compression device 100 may comprise a compression member 210 and a securement system 220. The securement system 220 may be coupled to the compression member 110 and be configured to facilitate attachment of the compression member 210 to a patient 50 so as to be over a compression site 60.

The securement system 220 may be configured to provide positional stability of the compression member 210 over the compression site 60. The securement system 220 may comprise a plurality of straps 225 extending away from the compression member 210. Each strap 225 may comprise a free end and may be coupled to the compression member 210 at a fixed end. The straps 225 may be generally elongate in shape, i.e., having a greater longitudinal length than width, wherein the length is defined as the distance extending away from the compression member 200. In some instances, one or more straps 225 may have a greater width than length. Other shapes and designs of the straps 225 are likewise within the scope of this disclosure. The width at the fixed end may be substantially equal to or greater than a cross-sectional dimension of the compression member 210, such as a diameter for example.

Though the example shown in the FIG. 9 and described below may include four straps, embodiments with more or fewer straps are likewise within the scope of this disclosure. Disclosure given below with respect to any specific number of straps (such as four straps) may be analogously applied to embodiments with more or fewer straps, including two, three, four, five, six, and so on.

As shown in FIG. 9, the plurality of straps 225 are collectively referred to with the reference numeral 225, while the four individual straps of the illustrated embodiment are designated with reference numerals **225*a*, 225*b*, 225*c*, and 225*d*. Disclosure regarding the size, shape, design, or other structure of any individual strap of the plurality of straps 225 may be applied to any other individual strap. Each strap may be configured to extend to and attach to specific areas of the skin of the patient. As such, each strap of the plurality of straps 225 may have different dimensions (length and width) or the straps 225 may have similar dimensions. While the straps 225*a*, 225*b*, 225*c*, and 225*d* are generally shown as straight, the straps 225 may comprise one or more curves. Similarly, the width of the straps 225 may vary along the length. The length (distance from the compression member 210 to the free end) of straps 225*a*, 225*c* may be between about 3 and 6 inches, between about 4 and 5 inches, about 4.5 inches, or longer than 6 inches. The width of each of the straps 225*a*, 225*c* may be between about 1 and 4 inches, between about 2 and 3 inches, or about 2.5 inches. The length (distance from the compression member 210 to the free end) of straps 225*b*, 225*d* may be between about 1 and 6 inches, between about 1 and 3 inches, or may be about 1.5 inches. The width of each of the straps 225*b*, 225*d*** may be between about 1 and 5 inches, between about 3 and 5 inches, or may be about 4 inches.

The straps 225 may comprise an adhesive 229 on an underside to facilitate attachment to the patient 50. The adhesive 229 may be distributed along the entire length and width of the straps 225. In some embodiments, a portion of the straps 225 may be free of adhesive 229 such as a portion adjacent the free end so as to facilitate removal of the strap 225 from the patient and/or a portion adjacent the fixed end so as to prevent adhesion to skin portions immediately adjacent the compression site 60. The adhesive 229 may be a pressure adhesive comprising a paper backing which upon removal enables the adhesive for securement of the strap 225 to the skin surface of the patient 50. In some embodiments, the straps 225 may be configured for the removal of defined portions of the backing paper while allowing other portions of the backing paper to remain intact. In such instances, a practitioner may selectively define attachment portions and non-attachment portions of the strap 225.

The plurality of straps 225 may be fixedly coupled to the compression member 210 such that each strap **225*a*, 225*b*, 225*c*, and 225*d* is fixed with regard to orientation with respect to the compression member 210 and the other straps 225. In other words, the straps 225 are configured such that they may extend away from the compression member 210 at a fixed direction or angle. Straps 225*a* and 225*c* may extend away from the compression member 210 in opposite directions, i.e., straps 225*a* and 225*c* may be disposed at 180 degrees with respect to each other and may define a first pair of straps 225. Similarly straps 225*b* and 225*d* may extend away from the compression member 210 in opposite directions, i.e., straps 225*b* and 225*d* may be disposed at 180 degrees with respect to each other and may define a second pair of straps 225. In some such embodiments, straps 225*a* and 225*c* may comprise one continuous member extending across the compression member 210 as may straps 225*b* and 225*d***.

Straps **225*a* and 225*c* may extend substantially along a longitudinal axis 211 of the compression member 210 as defined below. In some embodiments, the straps 225*a* and 225*c* may be directly in line with the longitudinal axis 211 and in other embodiments, the straps 225*a* and 225*c* may be disposed at an angle between with respect to the longitudinal axis 211. Straps 225*b* and 225*d* may be disposed in a direction transverse to straps 225*a* and 225*c*. In some embodiments, the straps 225*b* and 225*d* may be directly orthogonal with respect to straps 225***a* and 225*c* and in other embodiments, the straps 225*b* and 225*d* may be disposed at an angle between about 70 and 90 degrees, an angle between about 80 and 90 degrees, or an angle of about 85 degrees with respect to the straps 225*a* and 225*c*. Some embodiments of the compression device 200 may be configured to be placed on opposite sides of the body 50 and as such, may be defined as right hand or left hand versions. In such embodiments, the right and left hand versions may be symmetrical to each other (mirror images) or non-symmetrical.

The securement system 220 may also comprise a collar 227 extending away from a circumference of the compression member 210. Said another way, the straps 225 may couple to the compression member 210 such that a portion of straps 225 extends entirely around the circumference of the compression member 210 defining the collar 227 of strap material disposed about the circumference of the compression member 210. The collar 227 may facilitate attachment of the compression device 200 to the patient 50 prior to, and/or independent of, establishing tension in the straps 225. The collar 227 may also provide a coupling surface for additional straps to be applied as described below.

In some embodiments, the backing paper may be removed from different portions of the straps 225 to facilitate different functions during attachment of the compression device 200. As such, the backing paper may comprise breaks to facilitate removal of some portions while other portions remain intact. In some instances, the practitioner may prefer to remove the backing paper from the collar 227 and attach the collar 227 to the patient 50 first so as to establish the location of the compression member 210, and thereafter, remove the backing paper from the straps 225 and attach the straps 225 with tension to establish a downward force on the compression member 210.

The compression member 210 may be configured to apply compression to an elongate compression site 60 such as an elongate incision. As such, the compression member 210 may comprise a defined shape. The shape may be elongate such that the length is greater than the width. The shape of the compression member 210 may be defined by the shape of the top plate 230 which in some embodiments may correlate to the shape of the bladder 240. The shape of the top plate 230 may comprise substantially straight sides defining the width. Curved convex outer edges may connect the straight sides on each end of the top plate 230 and thereby define the length. The length of the top plate 230 may be between about 2 and 5 inches, between about 3 and 5 inches, or may be about 4 inches. The width of the top plate 230 may be between about 1.5 and 3 inches, between about 2 and 3 inches, or may be about 2.5 inches. The top plate 230 may be formed from a transparent or translucent material. As such, the top plate 230 may define a window 233 through which the practitioner may view the compression site 60 and/or the bladder 240. The shape of the window 233 may be defined by the shape of the top plate 230 such that the viewing area may extend substantially to the circumference of the top plate 230.

The bladder 240 may comprise a shape similar to the top plate 230 or the bladder 240 may have a different shape. The bladder may be oblong in shape such as an oval or ellipse. The length the bladder 240 may be between about 2 and 4 inches, between about 2.5 and 3.5 inches, or may be about 3 inches. The width of the bladder may be between about 1 and 2.5 inches, between about 1.5 and 2 inches, or may be about 1.75 inches. The size and configuration of the bladder 240 in combination with the manner of securement of the compression member 210 to the patient 50 may define a relationship between an internal pressure of the bladder 240 and a volume of air delivered to the bladder 240. In other words, a defined volume of air at atmospheric pressure delivered to the bladder 240 may define an internal pressure of the bladder 240. Application of the inflatable compression device 200 to the patient 50 may affect the relationship between the defined volume of air delivered to the bladder 240 and the resulting internal pressure of the bladder 240 because expansion of the bladder 240 is inhibited by contact of the bladder 240 with the compression site 60. In some embodiments, the Table 1 below may define the relationship between the volume of air delivered to the bladder 240 and the resulting range of internal pressure of the bladder 240 when the compression member 210 is secured to the patient 50 by the securement system 220.

TABLE 1

| Volume of Air Delivered to the Bladder 240 | Internal Pressure of the Bladder 240 |
|---|---|
| 20 ml | Between about 0.1 and 0.3 PSI or about 0.2 PSI |
| 40 ml | Between about 0.2 and 0.5 PSI or about 0.35 PSI |
| 60 ml | Between 0.4 and 0.6 PSI or about 0.5 PSI |

Similar to the bladder 240, a hemostasis enhancement substance 245 may be applied to an external surface of the bladder 240 so that upon placement of the compression device 200, the hemostasis enhancement substance 245 may contact an area of the patient's skin comprising the compression site 60 and thereby provide an enhanced hemostatic effect.

The compression device 200 may comprise a tube 260 coupled to the top plate 230 such that the tube 260 is in fluid communication with the bladder 240 at one end via the orifice 290 extending through the top plate 230. The tube 260 may be coupled to the top plate 230 at a location toward an outer edge of the top plate 230 and/or the bladder 240 so as to not obstruct visibility through the window 233. The tube 260 may be coupled to the top plate 230 such that at least a portion of the tube 260 extends along the surface of the top plate 230 or in other words, the tube 260 may be disposed substantially parallel to the top plate 230. A fluid port 250 may be coupled to the other end of the tube 260 so that the fluid port 250 is in fluid communication with the bladder 240. The tube 260 may provide flexibility between the fluid port 250 and the top plate 230 thus facilitating ease of connecting the inflation device 70 to the fluid port 250.

The tube 260 may be coupled to the top plate 230 so that the tube 260 is oriented in a manner to facilitate access to the fluid port 250. In some embodiments, the tube 260 may be oriented, and comprise sufficient length, such that the fluid port 250 is located near an opening in the patient's clothing when the compression device 200 is attached to the patient 50.

The inflation port 250 may comprise a valve 255 to facilitate inflation and deflation of the bladder 240 and containment of fluid within the bladder 240. The valve 255 may be configured to open and thereby allow fluid to flow through the inflation port 250 in direct response to coupling the inflation port 250 to an inflation device 70 such as a syringe for example. In similar fashion the valve 255 may be configured to close and prevent or minimize flow through the inflation port 250 in direct response to decoupling the inflation port 250 from the inflation device 70.

One exemplary procedure of use may include first placing the compression member 210 on the patient 50 in a specific or desired orientation with respect to the compression site 60. (As described above, in some instances the compression site 60 may be elongated or wider that it is tall, thus, in some instances an elongate shaped compression member 210 may be positioned to align with the compression site 60.) Once the orientation and position of the compression member 210 are established, the practitioner may remove the paper backing from the straps 225 and adhere the straps 225 to the patient 50.

Figure 10A:
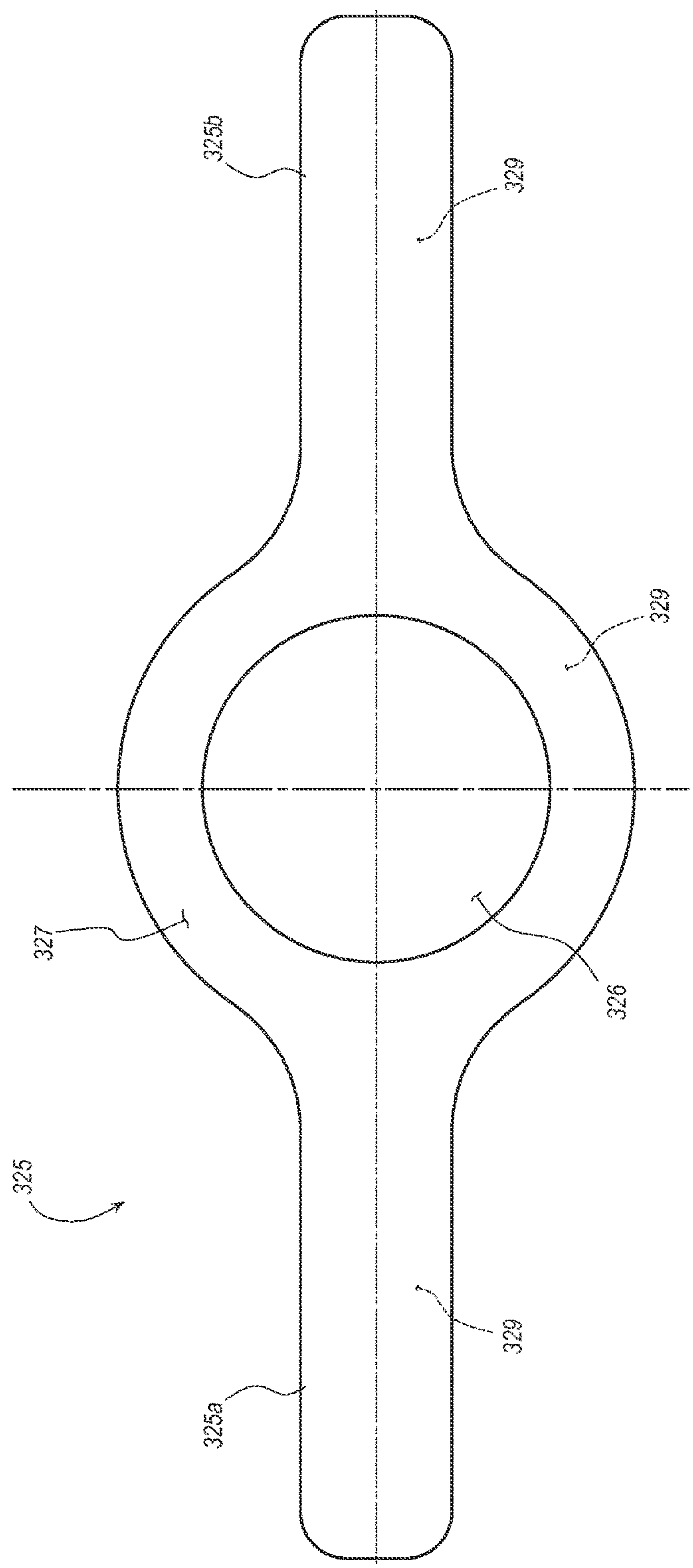
FIG. 10A is a top view of a strap that may be used in conjunction with the inflatable compression device of FIG. 9.

FIG. 10A shows a strap 325 which may be used in conjunction with the compression device 200 to further secure the compression member 210 to the skin of the patient 50 and further apply a downward force on the compression member 210 and thereby oppose upward displacement of compression member 210 which may be caused by inflation of the bladder 240. The strap 325 comprises opposing strap portions 325*a* and 325*b* extending away from an opening 326 toward the free ends of the strap 325. The strap 325 may extend across the opening 326 so as to establish a collar 327. The strap 325 may be configured to be disposed over the compression device 200 such that the opening 326 is in alignment with the window 233 and the collar 327 is disposed over the collar 227 (see FIG. 9). The length (distance between the opening 326 and the free end) of the strap 325 may be between about 3 and 12 inches, between about 3 and 10 inches, or may be about 8 inches. The width of the straps 325 may be between about 1 and 4 inches, between about 2 and 3 inches, or may be about 2.5 inches.

The strap 325 may comprise an adhesive 329 on an underside of the strap 325 including the collar 327. The collar 327 may define a coupling portion configured to attach the strap 325 to the inflatable compression device 200. The strap 325 may be coupleable to the inflatable compression device 200. More specifically, the strap 325 may be coupled to the collar 227 and/or straps 225. The adhesive 329 may be disposed on the entire underside of the strap 325 or there may be areas that are free of adhesive 329. For example, in some embodiments, the collar 327 and portions of the strap portions 325*a*, 325*b* adjacent the free ends may comprise adhesive 329 separated by a middle portion of the strap portions 325*a*, 325*b* that is free of adhesive 329. The adhesive 329 may be a pressure adhesive comprising a paper backing which upon removal enables the adhesive 329 for securement of the strap 325 to the skin surface of the patient 50. In some embodiments, the strap 325 may be configured for the removal of portions of the backing paper while allowing other portions of the backing paper to remain. In such instances, a practitioner may selectively define attachment portions and non-attachment portions of the strap 325. For example, a practitioner may remove the backing paper from the collar 327 so that the collar 327 may be attached to the compression device 200 while leaving the backing paper intact along the strap portions 325*a*, 325*b*. Thereafter, the practitioner may remove the backing paper from each strap portion 325*a*, 325*b* individually so that each strap portion 325*a*, 325*b* may be attached to the skin individually.

Figure 10B:
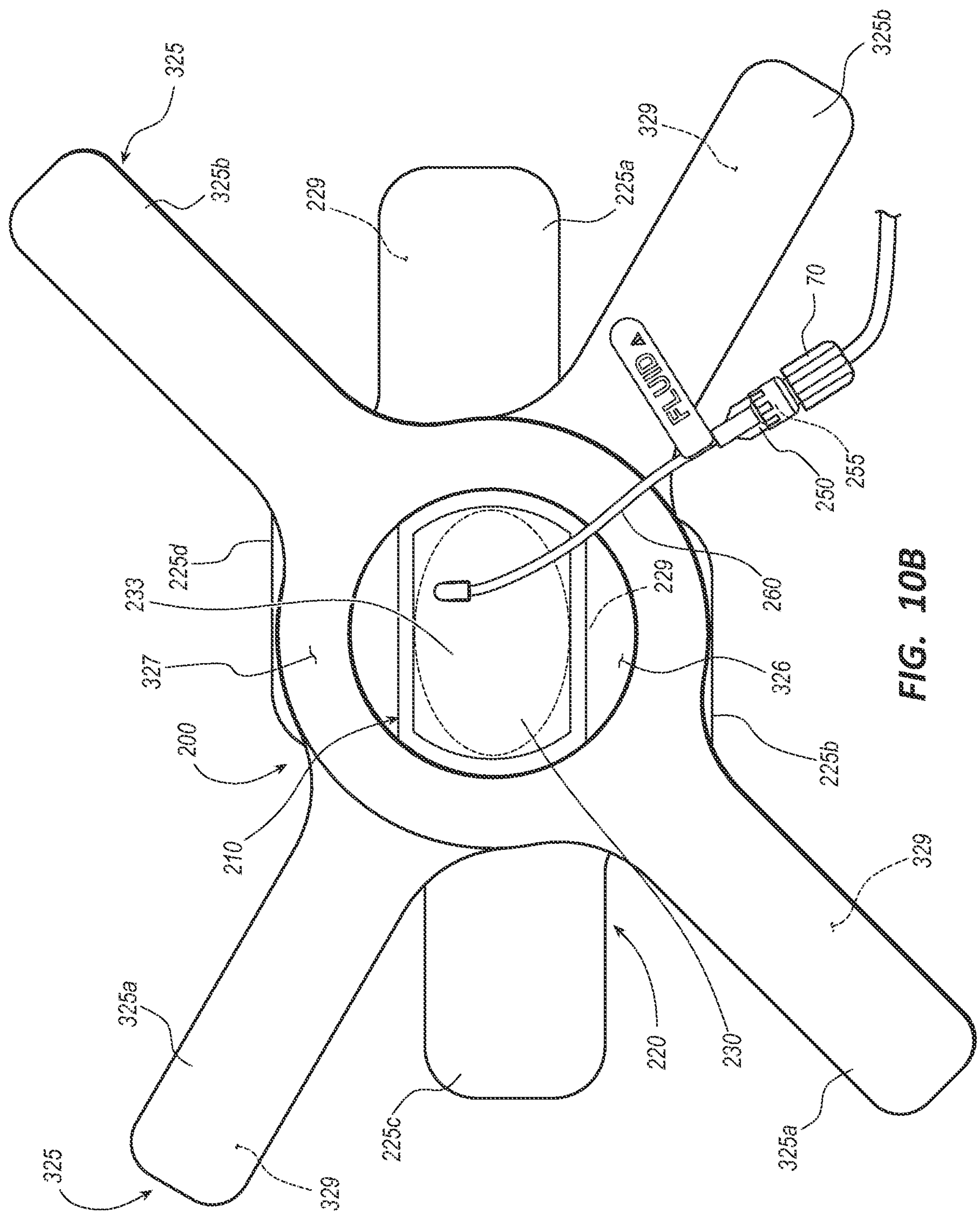
FIG. 10B is a top view of the inflatable compression device of FIG. 9 in combination with the strap of FIG. 10A.

As shown in FIG. 10B, a second strap 325 may be disposed over the first strap 325. The second strap 325 may be attached to the inflatable compression device 200 and to the skin surface of the patient 50 in a similar manner as described above with reference to the first strap 325.

In use, the practitioner may place the strap 325 over the compression device 200 in such a manner that the opening 326 is disposed around the compression member 210. As such, the opening 326 may be aligned with the window 233. The practitioner may pull strap portion 325*a* away from the compression device 200 so as to establish tension in the strap portion 325*a*, which may in some instances displace the compression device 200 in the direction of the strap portion 325*a*, and thereafter attach the strap portion 325*a* to the skin surface of the patient 50. The practitioner may thereafter pull the strap portion 325*b* away from the compression device 200 (in a direction opposite the strap portion 325*a*) so as to establish tension in the strap portion 325*b*, which may in some instances displace the compression device 200 in the direction of the strap portion 325*b*, and thereafter attach the strap portion 325*b* to the skin surface of the patient 50. Upon the attachment of both strap portions 325*a* and 325*b*, the tension in the strap portions 325*a*, 325*b* may substantially equalize so that the compression device 200 may resume its original position. This method of individually tensioning and attaching opposing strap portions may establish a greater tension in the strap portions 325*a* and 325*b* than the tension in straps 225. Furthermore, this method of individually tensioning and attaching opposing strap portions may establish pre-stressed portions of the skin of greater magnitude than may be established if the opposing strap portions were tensioned away from each other and attached to the skin surface of the patient 50 at the same time. As such, individually tensioning and attaching opposing strap portions may provide a greater downward force on the compression member 210. In some instances, the straps 325 may be oriented such that the strap portions 325*a* and/or 325*b* extend toward an area of the body where the skin is less loose such at the sternum area, shoulder area, etc.

As stated above in reference to FIG. 10B, in some instances, the practitioner may apply a second strap 325 over the first strap 325. The practitioner may tension the second strap 325 in a similar manner as the first strap 325. As the skin of the patient may be pre-stressed due to the tensioning of the first strap 325, the tension in the second strap 325 may be greater than the tension in the strap 325.

Figure 11A:
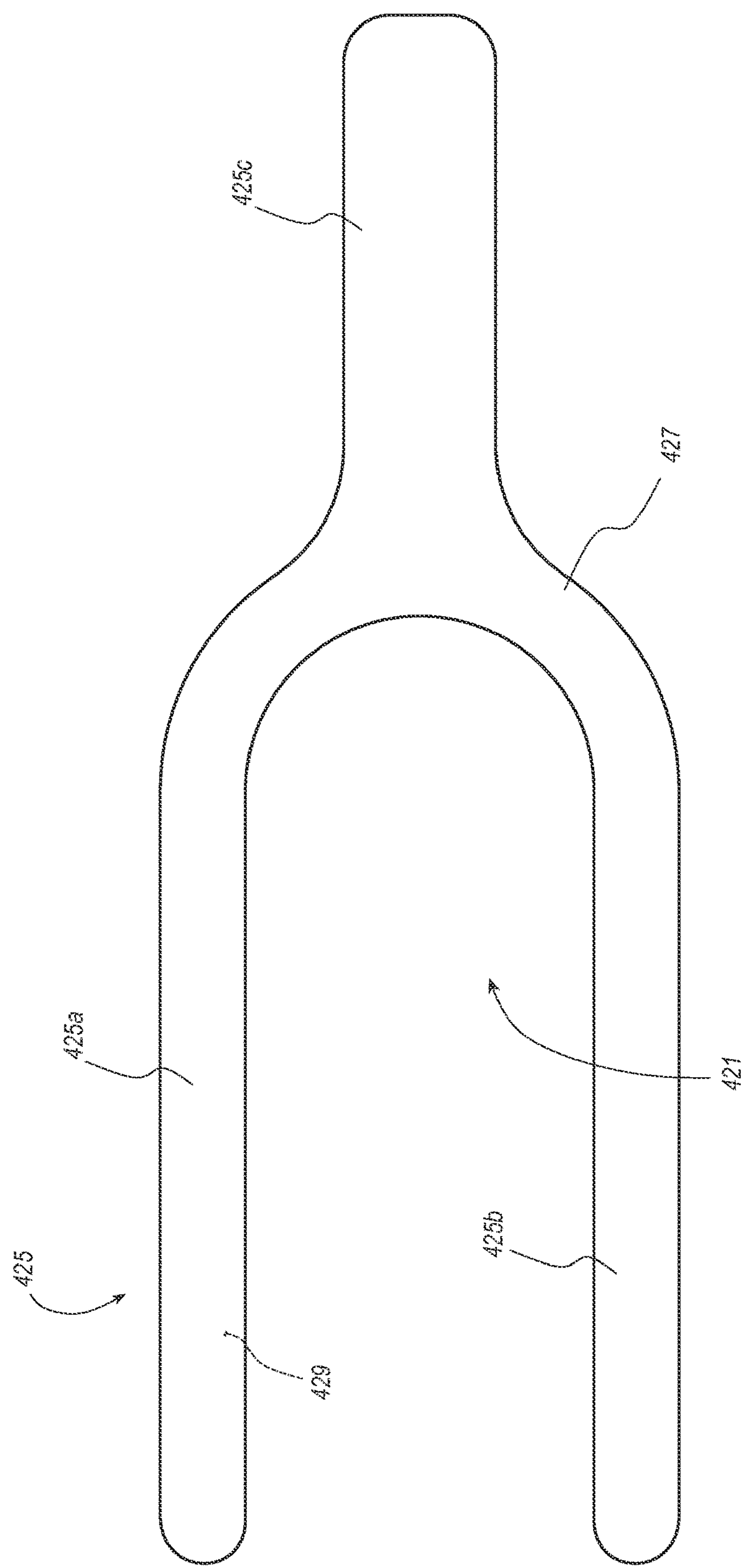
FIG. 11A is a top view of another embodiment of a strap that may be used in conjunction with the inflatable compression device of FIG. 9.

FIG. 11A shows a strap 425 which may be used in conjunction with the compression device 200 to further secure the compression member 210 to the skin of the patient 50 and further apply a downward force on the compression member 210 in opposition to upward displacement of compression member 210 as a result of inflation. In some instances, the strap 425 may be more effective in applying a downward force on the compression member 210 than the strap 325 described above. The strap 425 may comprise two parallel strap portions 425*a*, 425*b*, and an opposing strap portion 425*c* forming a two-pronged fork shape. Strap portions 425*a*, 425*b* may extend substantially parallel to one another in one direction and strap portion 425*c* may extend in a direction opposite to strap portions 425*a*, 425*b*. Strap portions 425*a*, 425*b* may in some embodiments not be parallel to one another. Strap portions 425*a*, 425*b* may be separated from one another defining a channel or opening 421 having a width substantially equal to the length of the compression member 210. The channel 421 comprises an open end adjacent the free end of the strap portions 425*a*, 425*b*. The strap portions 425*a*, 425*b*, and 425*c* are coupled together at a juncture defining a closed end of the channel 421. The closed end of the channel 421 may comprise about a half circular (full radius) at the juncture defining a collar 427 which may be disposed semi-annularly around the compression member 210. The strap portion 425*c* may be disposed on a line bisecting the channel 421.

Figure 11B:
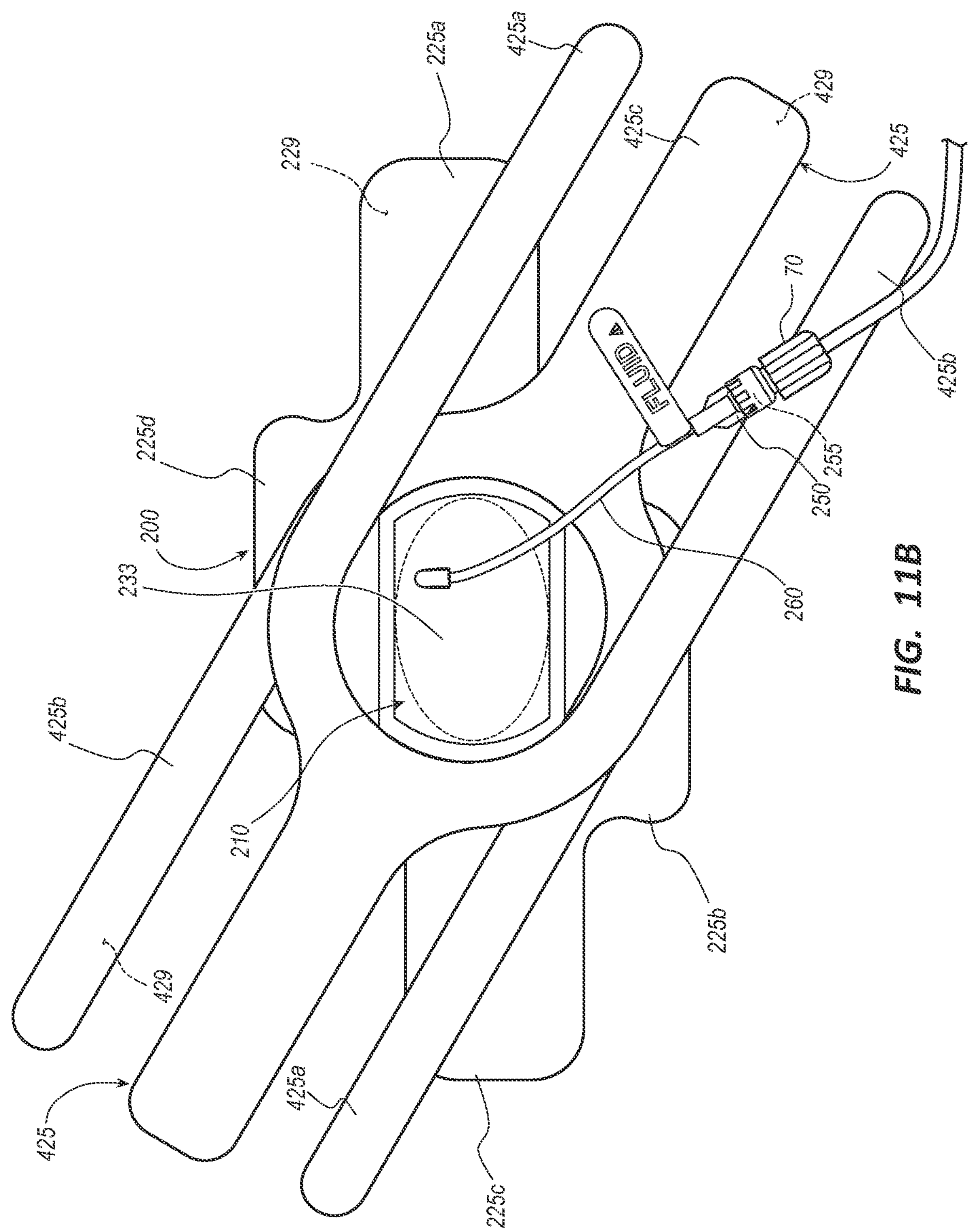
FIG. 11B is a top view of the inflatable compression device of FIG. 9 in combination with the strap of FIG. 11A.

FIG. 11B shows the strap 425 as may be used in conjunction with the compression device 200. The strap 425 may be configured to be disposed over the compression device 200 such that the collar 427 is disposed adjacent to the compression member 210 and extends about 180 degrees around the compression member 210 and specifically around the window 233. In some instances, a pair of straps 425 may be applied to the compression device 200 such that the two straps 425 are disposed in opposite orientations as further described below.

The straps 425 comprise adhesive 429 on an underside of the straps 425 including the collar 427. The adhesive 429 may be disposed on the entire underside of the straps 425 or there may be segments of the underside that are free of adhesive 429. For example, in some embodiments, the collar 427 and segments of the strap portions 425*a*, 425*b* adjacent the free ends may comprise adhesive 429 separated by middle segments of the strap portions 425*a*, 425*b*, and 425*c* that are free of adhesive 429. The adhesive 429 may be a pressure adhesive comprising a paper backing. In some embodiments, the straps 425 may be configured for the removal of portions of the backing paper while allowing other portions of the backing paper to remain. In such instances, a practitioner may selectively define attachment portions and non-attachment portions of the straps 425. For example, a practitioner may remove the backing paper from the collar 427 so that the collar 427 may be attached to the compression device 200 while leaving the backing paper intact along the strap portions 425*a*, 425*b*, and 425*c*. Thereafter, the practitioner may remove the backing paper from each of the strap portions 425*a*, 425*b*, and 425*c* individually so that each strap portion may be attached to the skin individually.

In use, one or more straps 425 may be applied to the compression device 200. In some instances, two straps 425 may be applied to the compression device 200 such that the straps 425 are disposed in opposite orientations as shown in FIG. 11B and further described below. In use, the practitioner may attach the compression device 200 to a patient 50 as described above and subsequently one or more straps 425. The practitioner may attach the straps 425 by pre-stressing the skin of the patient as follows. In some instances, the practitioner may attach strap portions 425*a* and 425*b* to the skin surface of the patient 50. Thereafter, the practitioner may establish tension in the strap 425 by pulling the strap portions 425*a* and 425*b* toward the compression device 200 thereby pulling the skin (as coupled to the straps 425*a* and 425*b*) toward the compression device 200 (pre-stressing a portion of the skin) and then attach the strap portion 425*c* to the skin surface of the patient 50 on the opposite side of the compression member 200 such that the channel or opening 421 straddles, or is otherwise aligned with, the compression member 210 and the collar 427 extends semi-annularly around the compression member 210 specifically the window 233. In some instances, a second strap 425 may be applied in a similar manner with the first strap 425 disposed in an opposite direction. The application of the second strap 425 may further add stress to the already pre-stressed portion of the skin. Pre-stressing the same portion of skin in this two-step manner may provide a greater downward force on the compression member 210 than otherwise might be provided by singularly pre-stressing two different skin portions. In some embodiments, the one or more straps 425 may be adhesively attached to the compression device 200 during application of the straps 425. In other embodiments, the one or more straps 425 may be coupled to the compression device 200 before use of the compression device 200 such as during manufacturing of the compression device 200. In some instances, a strap 425 may be oriented such that at least one of the strap portions 425*a*, 425*b*, and 425*c* extend toward an area of the body where the skin is less loose such as the sternum area, shoulder area, etc.

Figure 12:
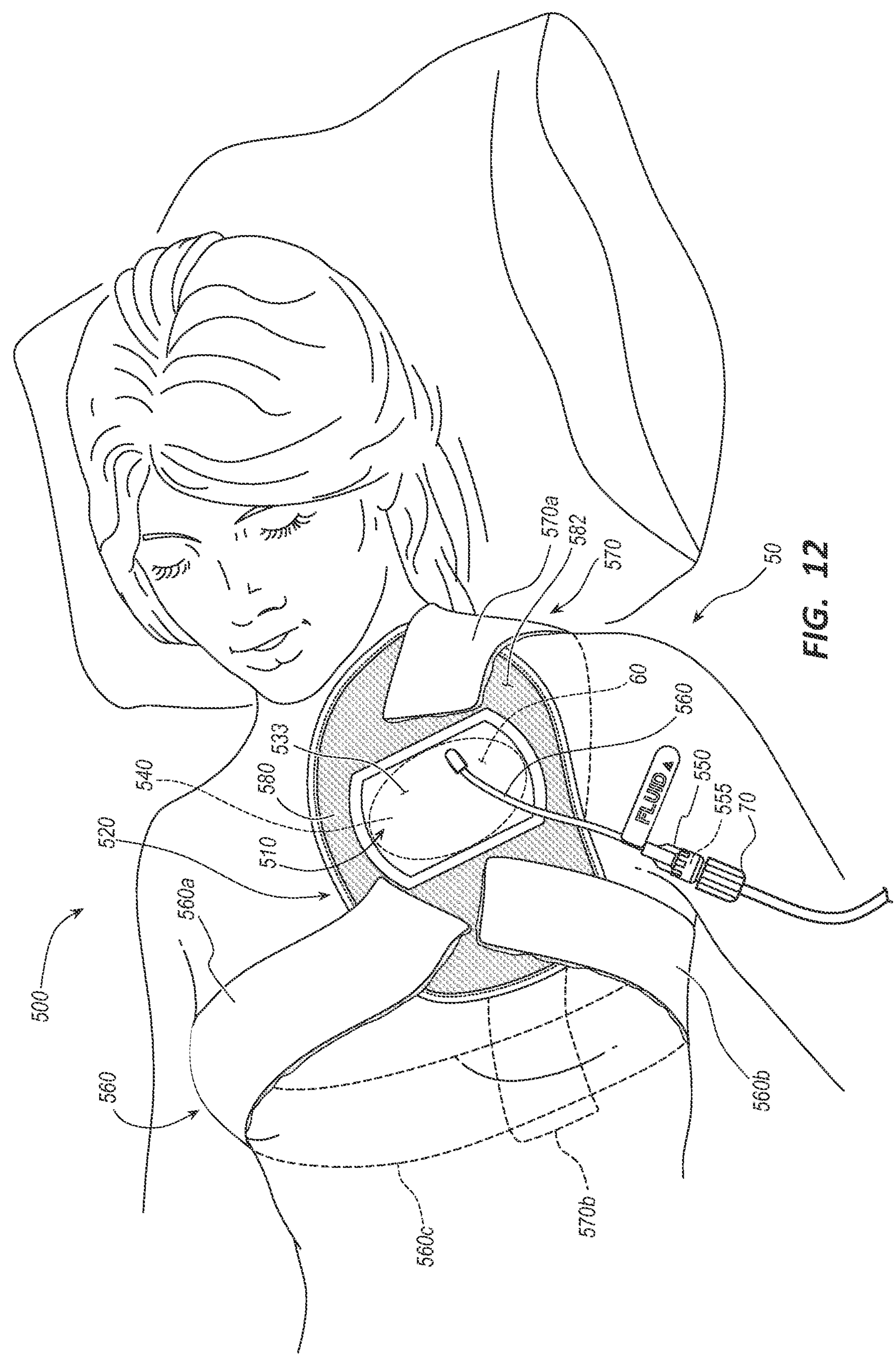
FIG. 12 is an illustration of an inflatable compression device in use on a patient according to another embodiment.
Figure 13:
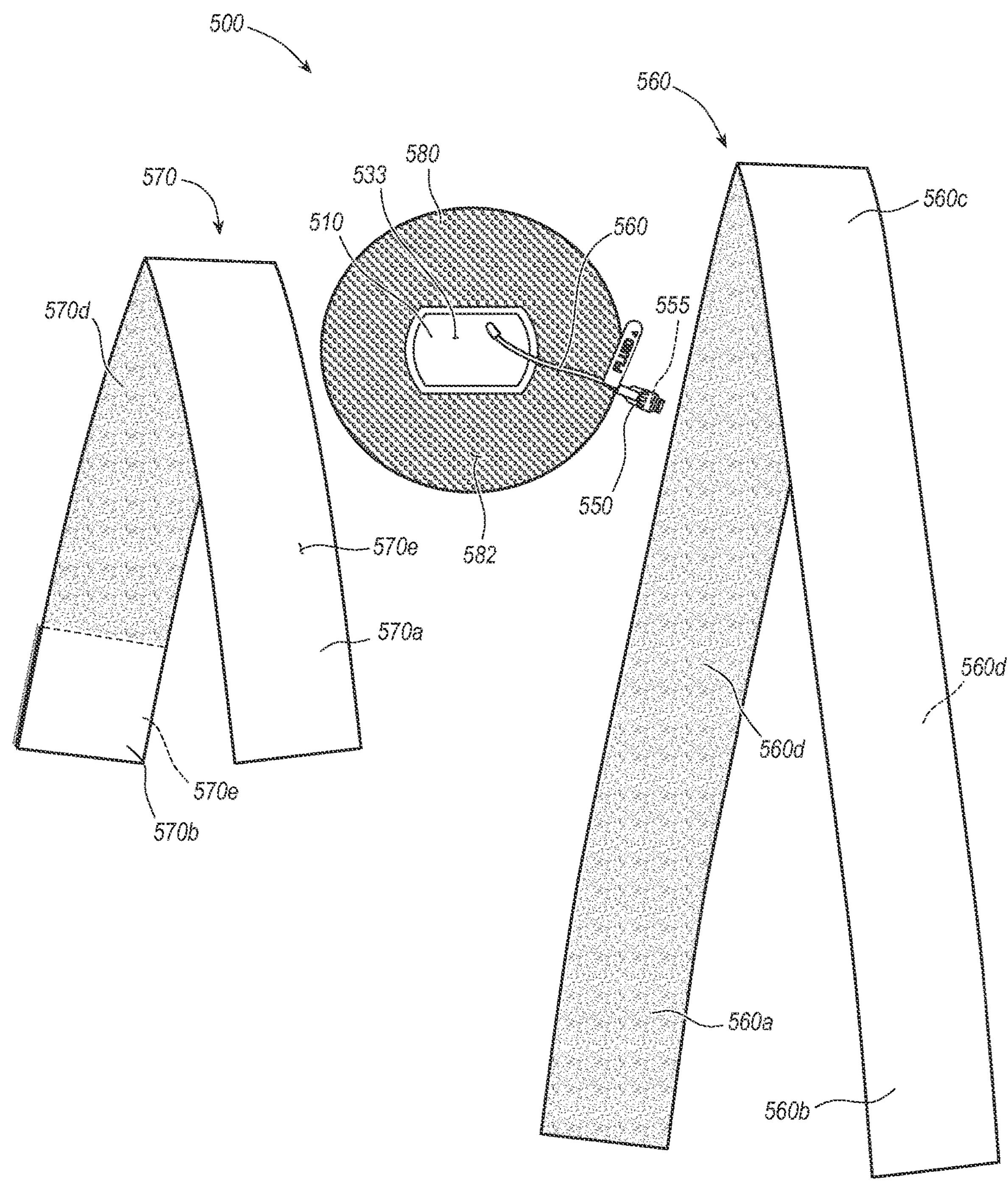
FIG. 13 is an illustration of the components of the inflatable compression device of FIG. 12.

FIG. 12 is an illustration of an inflatable compression device 500 in use on a patient 50 according to another embodiment and FIG. 13 is an illustration of components of the inflatable compression device 500. The inflatable compression device 500 comprises a compression member 510 that resembles the compression member 210 described above in certain respects. Accordingly, like features and/or components of the compression member 510 are designated with like reference numerals, with the leading digits incremented to "5." Relevant disclosure set forth above regarding similarly identified features and/or components of the compression member 510 thus may not be repeated hereafter.

The inflatable device 500 comprises a securement system 520. The securement system 520 comprises a collar 580 coupled to the compression member 510. In some embodiments, the collar 580 may be formed of a flexible material. The securement system 520 further comprises a first strap 560 and a second strap 570. The first strap 560 and the second strap 570 may be selectively coupleable to the collar 580 and each other. The collar 580, the first strap 560 and the second strap 570 may comprise any suitable releasable securement mechanism, such as a hook-and-loop fastening mechanism, pressure sensitive adhesives, buttons, buckles, magnets, snaps, clasps, etc. all of which are contemplated to be within the scope of this disclosure.

The collar 580 may extend away from the compression member 510 defining an annular coupling surface 582 disposed on the topside of the collar 580 such that the first strap 560 and the second strap 570 may be coupled to the collar 580 at a plurality of locations around the collar 580. In the illustrated embodiment, the coupling surface 582 may comprise a hook component of a hook-and-loop fastening mechanism. The hook component may extend across the coupling surface 582 so as to substantially cover the coupling surface 582. In some embodiments, the hook component may only be disposed at defined locations of the coupling surface 582. In some embodiments, the collar 580 may comprise an adhesive disposed on the underside of the collar 580 such that portions or a substantial entirety of the collar 580 may be attachable to the skin surface of the patient 50.

The first strap 560 may comprise a first end portion 560*a*, a second end portion 560*b*, and a middle portion 560*c*. The first strap 560 may comprise a total length sufficient to accommodate a maximum anticipated size of the patient 50. In other words, the total length of the first strap 560 may be sufficient to extend around the torso of the maximum anticipated patient size. In some instances, the first strap 560 may be disposed under the arms of the patient as shown in FIG. 12. In other instances, the first strap 560 may extends over one or both arms of the patient 50. The first strap 560 may comprise a loop component of the hook-and-loop fastening mechanism disposed on an underside 560*d* of the first strap 560 such that the first strap 560 is coupleable to the collar 580. The loop component may be disposed at certain portions of the first strap 560 such as the first end portion 560*a* and the second end portion 560*b* for example. Accordingly, the first strap 560 may be coupleable to the collar 580 at a plurality of locations along the first end portion 560*a* and the second end portion 560*b*. As such, the first strap 560 may be coupled to the collar 580 at a plurality of locations along the first strap 560. The first and second end portions 560*a*, 560*b* may extend inward from the ends of the first strap 560 so that the first strap 560 may accommodate a smallest anticipated patient size. In other words, the loop component may extend inward of the ends of the first strap 560 such that the first strap 560 may be coupled to the collar 580 when the first strap 560 is applied to the smallest anticipated patient 50. In such instances, the practitioner may trim excess length portions from the first end portion 560*a* and/or the second end portion 560*b*. As such, the first strap may be trimmable. The loop component may extend along a middle portion 560*c* of the first strap 560 to facilitate coupling of the first strap 560 to the second strap 570 as further described below. In some embodiments, the loop component may extend along an entire length and across the entire width of the first strap 560.

The second strap 570 may comprise a first end portion 570*a* coupleable to the collar 580 and a second end portion 570*b* coupleable to the first strap 560. Similar to the first strap 560, the second strap 570 may comprise a total length so as to accommodate a maximum size of the patient 50 and the second strap 570 may be trimmable to accommodate a minimum size of the patient 50. In some embodiments, first end portion 570*a* may extend along the length of the second strap 570 to the second end portion 570*b*. The second strap 570 may be configured to extend over a shoulder of the patient 50. Similar to the first strap 560, the second strap 570 may comprise a loop component disposed on an underside 570*d* of the second strap 570 extending along a length of the first end portion 570*a*. Accordingly, the second strap 570 may be coupled to the collar 580 at a plurality of locations along the second strap 570. The second strap 570 may also comprise a hook component of the hook-and-loop fastening mechanism disposed on a topside 570*e* of the second strap 570 extending along a length of the second end portion 570*b*. As such, the second strap 570 may be coupled to the first strap 560 at a plurality of locations along the second strap 570. The second strap 570 may also be coupled to a plurality of locations along the middle portion 560*c* of the first strap 560 and as such may be coupled to a plurality of locations along the first strap 560. In some embodiments, the second strap 570 may be fixedly coupled to the first strap 560.

The size and configuration of the bladder 540 in combination with the manner of securement of the compression member 510 to the patient 50 may define a relationship between an internal pressure of the bladder 540 and a volume of air delivered to the bladder 540. In other words, a defined volume of air at atmospheric pressure delivered to the bladder 540 may define an internal pressure of the bladder 540. Application of the inflatable compression device 500 to the patient 50 may affect the relationship between the defined volume of air delivered to the bladder 540 and the resulting internal pressure of the bladder 540 because expansion of the bladder 540 is inhibited by contact of the bladder 540 with the compression site 60. In some embodiments, Table 2 below may define the relationship between the volume of air delivered to the bladder 540 and the resulting range of internal pressure of the bladder 540 when the compression member 510 is secured to the patient 50 by the securement system 520.

TABLE 2

| Volume of Air Delivered to the Bladder 540 | Internal Pressure of the Bladder 540 |
|---|---|
| 20 ml | Between about 0.4 and 0.7 PSI or about 0.55 PSI |
| 40 ml | Between about 0.7 and 1.2 PSI or about 0.95 PSI |
| 60 ml | Between about 1 and 1.7 PSI or about 1.3 PSI |

An exemplary method of use of the inflatable compression device 500 may comprise one or more of the following steps or processes. A practitioner may position the compression member 510 over a compression site 60 and align a longitudinal axis of the compression member 510 with a longitudinal axis of the compression site. The practitioner may view the compression site 60 through the window 533 while positioning and aligning the compression member 510. The practitioner may extend the first strap 560 around the torso of the patient 50 and couple the first end portion 560*a* and the second end portion 560*b* to the collar 580. The practitioner may trim off excess portions from the first strap 560. The practitioner may couple the second strap 570 to the first strap 560, or more specifically, the practitioner may couple the second end portions 570*b* to the middle portion 560*c* of the first strap 560. When the first strap 560 is coupled to the second strap 570, the second strap 570 may be disposed underneath the first strap 560. The practitioner may extend the second strap 570 over the shoulder of the patient 50 and may couple the second strap 570 to the collar 580. The practitioner may trim off excess portions of the first strap 570.

The practitioner may fluidly couple an inflation device 70 to the inflation port 550 thereby opening the valve 555. The practitioner may inflate the compression member 510 to apply compression to the compression site 60 and thereby prevent, minimize, or control bleeding at the compression site 60. The practitioner may adjust the level of inflation according to a predetermined protocol or in response to a patient condition such as discomfort, bleeding, etc. The practitioner may visually observe the compression site 60 through the window 533 and adjust the level of inflation in response to visual observation made through the window 533. The practitioner may disconnect the inflation device 70 from the inflation port 550 thereby closing the valve 555. Once hemostasis is achieved, and/or sufficient healing has taken place, the securement system 520 may be separated from the compression member 510 and the compression member 510 removed from the patient 50.

Figure 14:
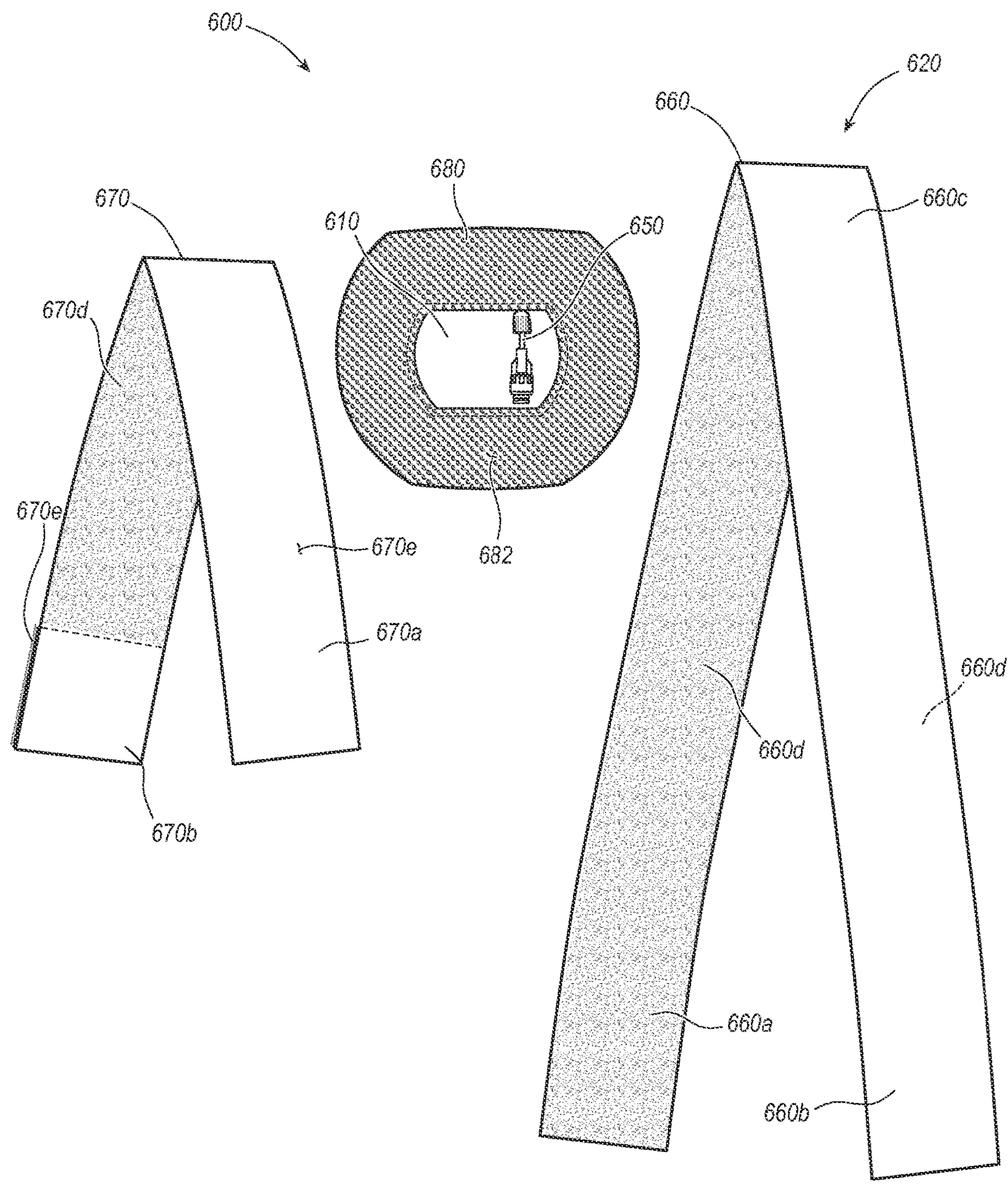
FIG. 14 is an illustration of inflatable compression device according to another embodiment.

FIG. 14 is an illustration of an inflatable compression device 600. The inflatable compression device 600 comprises a compression member 610 that resembles the compression member 510 described above in certain respects. Accordingly, like features and/or components of the compression member 610 are designated with like reference numerals, with the leading digits incremented to "6." Relevant disclosure set forth above regarding similarly identified features and/or components of the compression member 610 thus may not be repeated hereafter.

As illustrated in FIG. 14, the inflatable compression device 600 comprises a securement system 620. The securement system 620 comprises a collar 680 coupled to the compression member 610. In some embodiments, the collar 680 may be formed of a flexible material. The securement system 620 further comprises a first strap 660 and a second strap 670. The first strap 660 and the second strap 670 may be selectively coupleable to the collar 680 and each other. The collar 680, the first strap 660 and the second strap 670 may comprise any suitable releasable securement mechanism, such as a hook-and-loop fastening mechanism, pressure sensitive adhesives, buttons, buckles, magnets, snaps, clasps, etc. all of which are contemplated to be within the scope of this disclosure.

The collar 680 may extend away from the compression member 610 defining a racetrack shape with parallel straight sides and arcuate ends. A coupling surface 682 can be disposed on the topside of the collar 680 such that the first strap 660 and the second strap 670 may be coupled to the collar 680 at a plurality of locations around the collar 680.

In the illustrated embodiment, the coupling surface 682 may comprise a hook component of a hook-and-loop fastening mechanism. The hook component may extend across the coupling surface 682 so as to substantially cover the coupling surface 682. In some embodiments, the hook component may only be disposed at defined locations of the coupling surface 682.

The first strap 660 may comprise a first end portion 660*a*, a second end portion 660*b*, and a middle portion 660*c*. The first strap 660 may comprise a loop component of the hook-and-loop fastening mechanism disposed on an underside 660*d* of the first strap 660 such that the first strap 660 is coupleable to the hook component of the coupling surface 682. The loop component may extend along an entire length and across the entire width of the first strap 660.

The second strap 670 may comprise a first end portion 670*a* coupleable to the collar 680 and a second end portion 670*b* coupleable to the first strap 660. Similar to the first strap 660, the second strap 670 may comprise a loop component disposed on an underside 670*d* of the second strap 670. Accordingly, the second strap 670 may be coupled to the hook component of the coupling surface 682 at a plurality of locations along the second strap 670. The second strap 670 may also comprise a hook component of the hook-and-loop fastening mechanism disposed on a topside 670*e* of the second strap 670 extending along a length of the second end portion 670*b*. As such, the hook component of the second strap 670 may be coupled to the loop component of the first strap 660 at a plurality of locations along the first strap 660.

Figure 15A:
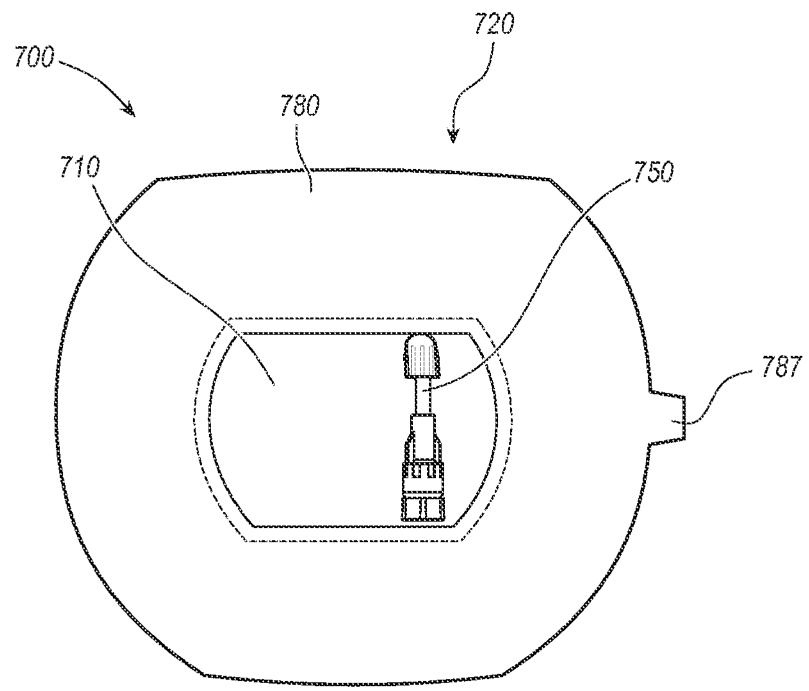
FIG. 15A is an illustration of inflatable compression device according to another embodiment.
Figure 15B:
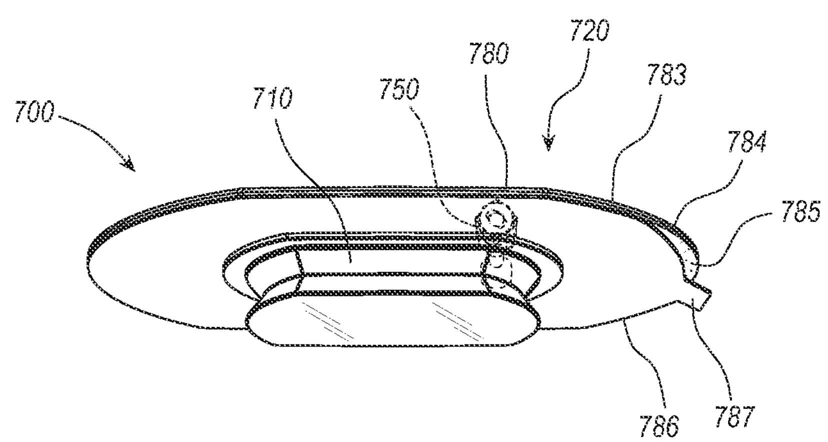
FIG. 15B is a side view of the inflatable compression device of FIG. 15A.

FIGS. 15A and 15B are an illustration of an inflatable compression device 700. The inflatable compression device 700 comprises a compression member 710 that resembles the compression member 210 of FIGS. 9, 10B, and 11B and described above in certain respects. Accordingly, like features and/or components of the compression member 210 are designated with like reference numerals, with the leading digits incremented to "7." Relevant disclosure set forth above regarding similarly identified features and/or components of the compression member 710 thus may not be repeated hereafter.

As illustrated in FIG. 15A, the inflatable compression device 700 comprises a securement system 720. The securement system 720 comprises a collar 780 coupled to the compression member 710. In certain embodiments, the securement system 720 may further comprise a first strap and a second strap similar to the straps of FIGS. 9-11C. The straps may be selectively coupleable to the collar 780 and each other. The collar 780 and the straps may comprise any suitable releasable securement mechanism, such as a hook-and-loop fastening mechanism, pressure sensitive adhesives, buttons, buckles, magnets, snaps, clasps, etc. all of which are contemplated to be within the scope of this disclosure.

The collar 780 may extend away from the compression member 710 defining a racetrack shape with parallel straight sides and arcuate ends. As illustrated in FIG. 15B, the collar may comprise a top layer 783, a bottom layer 784, an adhesive layer 785, and a release liner 786. The top layer 783 and bottom layer 784 can be formed of a suitable flexible material. The adhesive layer 785 can cover a bottom surface of the bottom layer 784. The adhesive layer 785 may comprise a pressure sensitive adhesive. The release liner 786 can be releasably coupled to the adhesive layer 785 to protect the adhesive layer 785 until the compression device is ready to use. A tab 787 can extend from any the release liner 786 to facilitate gripping of the release liner 786 for removal to expose the adhesive layer 785. When the adhesive layer 785 is exposed, the compression device 700 can be adhered to a patient's skin adjacent a surgical or incision site. In some embodiments, the top layer 783 and/or the bottom layer 784 may include a tab.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment. Similarly, it should be appreciated by one of skill in the art with the benefit of this disclosure that in the above description of embodiments, various features are sometimes grouped together in a single embodiment, figure, or description thereof for the purpose of streamlining the disclosure.

The invention claimed is:

1. An inflatable compression device, comprising:

a compression member configured to be coupled to a patient so as to apply compression to a compression site of the patient, the compression member comprising an inflatable bladder, wherein a level of compression is at least partially defined by an inflation pressure within the bladder; and a securement system comprising:

a collar coupled to the compression member; and one or more straps coupleable to the collar, wherein the securement system is configured to define a downward force of the compression member, wherein one of the one or more straps is detachably coupleable to the collar, wherein the collar is removably attachable to a circumference of the compression member and extends radially away from the compression member, and wherein the collar is more rigid than the one or more straps.

2. The compression device of claim 1, wherein the compression device is configured to apply compression to a compression site located on a torso of the patient.

3. The compression device of claim 1, wherein the compression member comprises an elongate shape so as to apply compression to an elongate compression site.

4. The compression device of claim 1, wherein the compression member further comprises a top plate and an inflation port, wherein the inflation port is coupled to a top surface of the top plate and the bladder is coupled to a bottom surface of the top plate, and wherein the inflation port is in fluid communication with the bladder.

5. The compression device of claim 4, wherein the top plate and the bladder define a window to facilitate visual observance of the compression site.

6. The compression device of claim 4, wherein the inflation port is coupled to the top plate via a tube, and wherein the inflation port and the tube are disposed substantially parallel to the top plate.

7. The compression device of claim 1, further comprising a therapeutic substance disposed on an outside surface of the bladder so as to be in contact with skin of the patient.

8. The compression device of claim 1, wherein the compression member comprises a groove disposed in the circumference of the compression member that is sized to receive the collar.

9. The compression device of claim 1, wherein the securement system comprises a plurality of collars that are removably attachable to the circumference of the compression member.

10. The compression device of claim 9, wherein the compression member comprises a plurality of grooves disposed in the circumference of the compression member, and wherein each groove is sized to receive one of the plurality of collars.

11. An inflatable compression device, comprising:

a compression member configured to be coupled to a patient so as to apply compression to a compression site of the patient, the compression member comprising an inflatable bladder, wherein a level of compression is at least partially defined by an inflation pressure within the bladder; and a securement system comprising:

a collar coupled to the compression member, a first strap and a second strap coupleable to the collar, wherein the securement system is configured to define a downward force of the compression member, and wherein the first strap and the second strap each comprise two substantially parallel strap portions that are continuous with an opposing strap portion forming a two-pronged fork shape, the two substantially parallel strap portions form a channel with an open end and a closed end that is defined at a juncture of the two substantially parallel strap portions and the opposing strap portion forming a half circular shape that is disposed around the compression member.

12. The inflatable compression device of claim 11, wherein the first strap and the second strap are attachable to the collar at any of a plurality of locations around the collar.

13. The inflatable compression device of claim 12, wherein the collar comprises a hook component of a hook-and-loop fastening mechanism, and wherein each of the first strap and the second strap comprises a loop component of the hook-and-loop fastening mechanism.

14. The inflatable compression device of claim 13, wherein the second strap further comprises the hook component of the hook-and loop fastening mechanism; and wherein the second strap is coupleable to the first strap.

15. The inflatable compression device of claim 11, wherein a back side of the first and second strap comprise adhesive to couple the first and second strap to skin of the patient.

16. A method of applying compression to a compression site located on a torso of a patient, comprising:

providing a compression device comprising:

an inflatable compression member; and a securement system configured to secure the compression member to the patient, the securement system comprising:

a collar removably attachable to the compression member; and one or more straps removably attachable to the collar;

coupling the collar to a circumference of the compression member;

placing the compression member over the compression site on the torso of the patient while visually observing the compression site through a window of the compression member;

securing the compression member to the patient by wrapping a first strap of the securement system around the torso of the patient; and inflating the compression member so as to establish a desired compression on the compression site.

17. The method of claim 16, further comprising aligning a longitudinal axis of the compression member with a longitudinal axis of the compression site while visually observing the compression site through the window.

18. The method claim 16, further comprising adjusting the inflation of the compression member in response to visual observation of the compression site through the window after inflating the compression member so as to establish a desired compression on the compression site.

* * * * *